US012805969B2

(12) United States Patent
Schneider

(10) Patent No.: US 12,805,969 B2
(45) Date of Patent: Nov. 24, 2026

(54) OPTICAL FIBER SHAPE SENSING

(71) Applicant: Northern Digital Inc., Waterloo (CA)

(72) Inventor: Mark Robert Schneider, Williston, VT (US)

(73) Assignee: Northern Digital Inc., Waterloo (CA)

(*) Notice: Subject to any disclaimer, the term of this patent is extended or adjusted under 35 U.S.C. 154(b) by 344 days.

(21) Appl. No.: 18/503,458

(22) Filed: Nov. 7, 2023

(65) Prior Publication Data

US 2024/0148466 A1 May 9, 2024

Related U.S. Application Data

(60) Provisional application No. 63/423,755, filed on Nov. 8, 2022.

(51) Int. Cl.
*A61B 90/00* (2016.01)
*G01B 11/16* (2006.01)

(52) U.S. Cl.
CPC .............. *A61B 90/37* (2016.02); *G01B 11/18* (2013.01); *A61B 2090/374* (2016.02)

(58) Field of Classification Search
None
See application file for complete search history.

(56) References Cited

U.S. PATENT DOCUMENTS

| | | | |
|---|---|---|---|
| 4,951,674 | A | 8/1990 | Zanakis et al. |
| 5,377,678 | A | 1/1995 | Dumoulin et al. |
| 6,545,760 | B1 | 4/2003 | Froggatt et al. |
| 7,742,799 | B2 | 6/2010 | Mueller et al. |
| 7,772,541 | B2 | 8/2010 | Froggatt et al. |
| 7,781,724 | B2 | 8/2010 | Childers et al. |
| 7,813,599 | B2 | 10/2010 | Moore |
| 8,123,400 | B2 | 2/2012 | Andrejco et al. |
| 8,183,520 | B2 | 5/2012 | Prisco |
| 8,276,462 | B2 | 10/2012 | Tao et al. |
| 8,515,215 | B2 | 8/2013 | Younge et al. |
| 8,520,986 | B2 | 8/2013 | Dailey |
| 8,746,076 | B2 | 6/2014 | Rogge et al. |

(Continued)

FOREIGN PATENT DOCUMENTS

| | | |
|---|---|---|
| CA | 2324894 | 4/2001 |
| JP | S61-84571 A | 4/1986 |

OTHER PUBLICATIONS

Amirsolaimani et al. “High sensitivity magnetometer using nanocomposite polymers with large magneto-optic response,” Optics Letters, Oct. 2018, 43(19):4615-4618.

(Continued)

*Primary Examiner* — Jerry Rahll
(74) *Attorney, Agent, or Firm* — Fish & Richardson P.C.

(57) ABSTRACT

A computing device implemented method includes receiving data representing strains experienced at multiple positions along a fiber, the fiber being positioned within a surgical theater, determining a shape of the fiber from the received data representing the stains experienced at the multiple positions along the fiber by using a machine learning system, the machine learning system being trained using data representing shapes of fibers and data representing strains at multiple positions along each of the fibers, and representing the determined shape as functions of an orientation of a center of the fiber, a first radial axis of the fiber, and a second radial axis of the fiber.

20 Claims, 12 Drawing Sheets

(56) References Cited

U.S. PATENT DOCUMENTS

| | | | |
|---|---|---|---|
| 8,773,650 B2 | 7/2014 | Froggatt et al. | |
| 8,970,845 B1 | 3/2015 | Chen et al. | |
| 9,200,971 B2 | 12/2015 | Froggatt et al. | |
| 9,417,057 B2 | 8/2016 | T Hooft et al. | |
| 9,423,311 B2 | 8/2016 | Moslehi | |
| 9,441,954 B2 | 9/2016 | Ramamurthy et al. | |
| 9,494,809 B2 | 11/2016 | Yamada et al. | |
| 9,693,707 B2 | 7/2017 | Chan et al. | |
| 9,733,336 B2 | 8/2017 | Shen et al. | |
| 9,757,034 B2 | 9/2017 | Desjardins et al. | |
| 9,784,569 B2 | 10/2017 | Froggatt et al. | |
| 9,841,269 B2 | 12/2017 | Froggatt et al. | |
| 9,861,271 B2 | 1/2018 | Liu et al. | |
| 9,918,659 B2 | 3/2018 | Chopra et al. | |
| 9,958,605 B2 | 5/2018 | Wei et al. | |
| 10,178,945 B2 | 1/2019 | Kuboi et al. | |
| 10,317,196 B2 | 6/2019 | Laine et al. | |
| 10,376,321 B2 | 8/2019 | DiMaio et al. | |
| 10,378,883 B2 | 8/2019 | Gifford et al. | |
| 10,422,631 B2 | 9/2019 | Reaves et al. | |
| 10,531,828 B2 | 1/2020 | Bell et al. | |
| 10,551,170 B2 | 2/2020 | T Hooft et al. | |
| 10,610,306 B2 | 4/2020 | Chopra et al. | |
| 10,612,911 B1 | 4/2020 | Pena, III et al. | |
| 10,663,290 B1 | 5/2020 | Tongue et al. | |
| 10,775,157 B2 | 9/2020 | Gifford et al. | |
| 10,859,411 B2 | 12/2020 | Alemohammad et al. | |
| 10,869,603 B2 | 12/2020 | Millett et al. | |
| 10,905,855 B2 | 2/2021 | Leo | |
| 11,007,027 B2 | 5/2021 | Fuerst et al. | |
| 11,035,699 B2 | 6/2021 | Froggatt et al. | |
| 11,079,217 B2 | 8/2021 | Van Putten et al. | |
| 11,173,597 B2 | 11/2021 | Rabindran et al. | |
| 11,353,524 B1 | 6/2022 | Strutner et al. | |
| 2004/0152970 A1 | 8/2004 | Hunter et al. | |
| 2005/0187463 A1 | 8/2005 | Quistgaard et al. | |
| 2006/0082789 A1 | 4/2006 | Goldbach | |
| 2006/0103380 A1 | 5/2006 | Kochergin et al. | |
| 2010/0030063 A1 | 2/2010 | Lee et al. | |
| 2010/0215311 A1* | 8/2010 | Moore | G01B 11/18 356/73.1 |
| 2010/0317964 A1 | 12/2010 | Hendriks et al. | |
| 2011/0119023 A1* | 5/2011 | Duindam | A61B 34/70 702/150 |
| 2011/0319714 A1* | 12/2011 | Roelle | A61B 1/0051 600/118 |
| 2012/0001625 A1 | 1/2012 | Yamada et al. | |
| 2013/0102878 A1 | 4/2013 | Burg et al. | |
| 2013/0131503 A1 | 5/2013 | Schneider et al. | |
| 2014/0070802 A1 | 3/2014 | Yamada et al. | |
| 2016/0101263 A1 | 4/2016 | Blumenkranz et al. | |
| 2016/0370177 A1 | 12/2016 | Laine et al. | |
| 2017/0238996 A1 | 8/2017 | Frame et al. | |
| 2017/0325895 A1 | 11/2017 | Krimsky | |
| 2018/0256262 A1 | 9/2018 | Duindam et al. | |
| 2018/0289927 A1 | 10/2018 | Messerly | |
| 2019/0000562 A1 | 1/2019 | Thienphrapa et al. | |
| 2019/0029759 A1* | 1/2019 | Mcdonell | A61B 34/20 |
| 2019/0143506 A1 | 5/2019 | Rabindran et al. | |
| 2019/0234726 A1 | 8/2019 | Gifford et al. | |
| 2019/0307995 A1 | 10/2019 | Flexman et al. | |
| 2019/0390985 A1 | 12/2019 | Kwok et al. | |
| 2020/0188036 A1 | 6/2020 | Ding et al. | |
| 2020/0188038 A1 | 6/2020 | Donhowe et al. | |
| 2020/0214598 A1 | 7/2020 | Li et al. | |
| 2020/0264018 A1 | 8/2020 | Froggatt et al. | |
| 2021/0038322 A1 | 2/2021 | Thompson et al. | |
| 2021/0045814 A1 | 2/2021 | Thompson et al. | |
| 2021/0116265 A1 | 4/2021 | Takakuma et al. | |
| 2021/0128250 A1 | 5/2021 | Chav et al. | |
| 2021/0156676 A1 | 5/2021 | Messerly et al. | |
| 2021/0298680 A1 | 9/2021 | Sowards et al. | |
| 2021/0378759 A1 | 12/2021 | Komp et al. | |
| 2021/0402144 A1 | 12/2021 | Messerly et al. | |
| 2022/0071589 A1 | 3/2022 | Sowards et al. | |
| 2022/0233246 A1 | 7/2022 | Misener et al. | |
| 2023/0036150 A1 | 2/2023 | Wiles et al. | |
| 2023/0081198 A1* | 3/2023 | Sowards | A61B 5/346 600/302 |
| 2024/0060770 A1 | 2/2024 | Ha et al. | |
| 2024/0335237 A1 | 10/2024 | Sowards et al. | |
| 2024/0382129 A1 | 11/2024 | Schneider et al. | |

OTHER PUBLICATIONS

Wikipedia.org [online], "Dielectric," available on or before May 23, 2022, via Internet Archive: Wayback Machine URL<https://web.archive.org/web/20220523185612/https://en.wikipedia.org/wiki/Dielectric>, retrieved on May 14, 2024, URL<https://en.wikipedia.org/wiki/Dielectric>, 13 pages.

Wikipedia.org [online], "Gyroelectromagnetism," available on or before Jun. 16, 2020, via Internet Archive: Wayback Machine URL<https://web.archive.org/web/20200616174223/https://en.wikipedia.org/wiki/Gyroelectromagnetism>, retrieved on May 14, 2024, URL<https://en.wikipedia.org/wiki/Gyroelectromagnetism>, 1 page.

Wikipedia.org [online], "Light" available on or before May 24, 2022, via Internet Archive: Wayback Machine URL<https://web.archive.org/web/20220324071627/https://en.wikipedia.org/wiki/Light>, retrieved on May 14, 2024, URL<https://en.wikipedia.org/wiki/Light>, 13 pages.

Wikipedia.org [online], "Magnetic field," available on or before May 24, 2022, via Internet Archive: Wayback Machine URL<https://web.archive.org/web/20220324083432/https://en.wikipedia.org/wiki/Magnetic_field>, retrieved on May 14, 2024, URL<https://en.wikipedia.org/wiki/Magnetic field>, 30 pages.

Wikipedia.org [online], "Magneto-optic effect," available on or before May 12, 2022, via Internet Archive: Wayback Machine URL<https://web.archive.org/web/20220512061613/https://en.wikipedia.org/wiki/Magneto-optic_effect>, retrieved on May 14, 2024, URL<https://en.wikipedia.org/wiki/Magneto-optic effect>, 4 pages.

Wikipedia.org [online], "Permittivity," available on or before May 12, 2022, via Internet Archive: Wayback Machine URL<https://web.archive.org/web/20220512101334/https://en.wikipedia.org/wiki/Permittivity>, retrieved on May 14, 2024, URL<https://en.wikipedia.org/wiki/Permittivity>, 13 pages.

Wikipedia.org [online], "Physics," available on or before May 24, 2022, via Internet Archive: Wayback Machine URL<https://web.archive.org/web/20220324083216/https://en.wikipedia.org/wiki/Physics>, retrieved on May 14, 2024, URL<https://en.wikipedia.org/wiki/Physics>, 27 pages.

Wikipedia.org [online], "Polarization," available on or before May 24, 2022, via Internet Archive: Wayback Machine URL<https://web.archive.org/web/20220324042832/https://en.wikipedia.org/wiki/Polarization_(waves)>, retrieved on May 14, 2024, URL<https://en.wikipedia.org/wiki/Polarization_(waves)>, 25 pages.

Wikipedia.org [online], "Tensor," available on or before May 20, 2022, via Internet Archive: Wayback Machine URL<https://web.archive.org/web/20220520184616/https://en.wikipedia.org/wiki/Tensor>, retrieved on May 14, 2024, URL<https://en.wikipedia.org/wiki/Tensor>, 21 pages.

Wikipedia.org [online], "Transparency and translucency," available on or before May 25, 2022, via Internet Archive: Wayback Machine URL<https://web.archive.org/web/20220525102539/https://en.wikipedia.org/wiki/Transparency_and_translucency>, retrieved on May 14, 2024, URL<https://en.wikipedia.org/wiki/Transparency_and_translucency>, 11 pages.

Jäckle et al., "Fiber optical shape sensing of flexible instruments for endovascular navigation," CoRR, Submitted on Jun. 25, 2019, arXiv:1908.02120, 12 pages.

Xu et al., "Shape Sensing with Rayleigh Backscattering Fibre Optic Sensor," Sensors, Jul. 21, 2020, 20(14):1-19.

Abiodun et al., "State-of-the-art in artificial neural network applications: A survey," Heliyon, Nov. 13, 2018, 4(11):1-41.

(56) References Cited

OTHER PUBLICATIONS

Arm.com [online], "Arm AI: Bringing AI Technologies to Life," 2023, retrieved on Feb. 8, 2023, retrieved from URL<https://www.arm.com/products/silicon-ip-cpu/ai-platform>, 12 pages.
Boccaccio et al., "Calibration of a Fiber Bragg Grating as Ultra-Sensitive Strain Gauge," LNL Annual Report, Appl., Gen. and Interdisc. Phys. Instrumentation, 2010, 191-192.
Bock et al., "Automatic calibration of a fiber-optic strain sensor using a self-learning system," IEEE Transactions on Instrumentation and Measurement, Apr. 1994, 43(2):341-346.
Broomhead et al., "Multivariable Functional Interpolation and Adaptive Networks," Complex Systems, 1988, 2:321-355.
Cheng et al., "Calibrating static measurement data from distributed fiber optics by the integration of limited FBG sensors based on the extended kernel regression method," Measurement Science and Technology, Sep. 17, 2019, 30(12):125102 (abstract only).
Coral.ai [online], "Products: Helping you bring local AI to applications from prototype to production," 2020, retrieved on Feb. 8, 2020, retrieved from URL<https://coral.ai/products/>, 19 pages.
Ding et al., "Distributed Optical Fiber Sensors Based on Optical Frequency Domain Reflectometry: A review," Sensors, Apr. 3, 2018, 31 pages.
Duncan et al., "High-accuracy fiber-optic shape sensing," Proc. SPIE 6530, Sensor Systems and Networks: Phenomena, Technology, and Applications for NDE and Health Monitoring, Apr. 10, 2007, 65301S, 11 pages (abstract only).
fbgs.com [online], "FBG Principle," available on or before Jun. 14, 2021, retrieved on Jan. 10, 2023, retrieved from URL<https://fbgs.com/technology/fbg-principle/>, 8 pages.
Floris et al., "Fiber Optic Shape Sensors: A comprehensive review," Optics and Lasers in Engineering, Apr. 2021, 32 pages.
Galloway et al., "Fiber Optic Shape Sensing for Soft Robotics," Soft Robotics, Oct. 2019, 6(5):671-684.
Hornik, "Multilayer Feedforward Networks are Universal Approximators," Neural Networks, 1989, 2(5):359-366.
IBM.com [online], "What is a neural network?," Dec. 16, 2021, retrieved on Feb. 8, 2023, retrieved from URL<https://www.ibm.com/topics/neural-networks>, 11 pages.
ibm.com [online], "What is machine learning?," Oct. 12, 2020, retrieved on Feb. 8, 2020, retrieved from URL<https://www.ibm.com/topics/machine-learning>, 13 pages.
Inaccel.com [online], "CPU, GPU, FPGA or TPU: Which one to choose for my Machine Learning training?," Dec. 17, 2018, retrieved on Feb. 8, 2023, retrieved from URL<https://inaccel.com/cpu-gpu-fpga-or-tpu-which-one-to-choose-for-my-machine-learning-training/>, 9 pages.
Intel.com [online], "FPGA vs. GPU for Deep Learning," 2020, retrieved on Feb. 8, 2023, retrieved from URL<https://www.intel.com/content/www/us/en/artificial-intelligence/programmable/fpga-gpu.html>, 6 pages.
Issatayeva et al., "Design and analysis of a fiber-optic sensing system for shape reconstruction of a minimally invasive surgical needle." Sci Rep., Apr. 2021, 11(1):8609, 12 pages.
Jäckle et al., "3D Catheter Guidance including Shape Sensing for Endovascular Navigation," Proceedings vol. 11315, Medical Imaging 2020: Image-Guided Procedures, Robotic Interventions, and Modeling, Mar. 16, 2020, 9 pages.
Jäckle et al., "Three-dimensional guidance including shape sensing of a stentgraft system for endovascular aneurysm repair," International Journal of Computer Assisted Radiology and Surgery, May 7, 2020, 15:1033-1042 (abstract only).
Kautzman et al., "Calibration and Testing of Distributed Fiber Optic Sensors for Detection of High Energy Radiation," Journal of Directed Energy, Oct. 2018, 15 pages.
Khan et al., "Multi-core Optical Fibers with Bragg Gratings as Shape Sensor for Flexible Medical Instruments," IEEE Sensors Journal, Jul. 15, 2019, 19(14):5878-5884.
Klug et al., "Test and calibration of 20 FBG based strain transducers," Materials Science, Jul. 1, 2015, 11 pages.
Lally et al., "Fiber optic shape sensing for monitoring of flexible structures," Proc. SPIE 8345, Sensors and Smart Structures Technologies for Civil, Mechanical, and Aerospace Systems 2012, Apr. 6, 2012, 83452Y, 9 pages (abstract only).
Lazarev et al., "Fiber Bragg gratings strain measuring system and a sensor calibration setup based on mechanical nanomotion transducer," Proc. of SPIE vol. 10329, Jun. 26, 2017, 103292F-1, 7 pages.
Liang et al., "A Comprehensive Study of Optical Frequency Domain Reflectometry," IEEE Access, vol. 9, Jan. 2021, 22 pages.
Miller et al., "Shape sensing using distributed fiber optic strain measurements," Proc. SPIE 5502, Second European Workshop on Optical Fibre Sensors, Jun. 9, 2004, 4 pages (abstract only).
Monet et al., "High-Resolution Optical Fiber Shape Sensing of Continuum Robots: A Comparative Study," 2020 IEEE International Conference on Robotics and Automation (ICRA), May 31-Aug. 31, 2020, 8877-8883 (abstract only).
Moore et al., "Shape sensing using multi-core fiber optic cable and parametric curve solutions," Opt. Express, Jan. 30, 2012, 20(3): 2967-2973.
Pan et al., "A Survey on Transfer Learning," IEEE Transactions on Knowledge and Data Engineering, Oct. 2010, 22(10):1345-1359.
Park et al., "Universal Approximation Using Radial-Basis-Function Networks," Neural Computation, Jun. 1991, 3(2):246-257.
Primo.ai [online], "Processing Units—CPU, GPU, APU, TPU, VPU, FPGA, QPU," Nov. 16, 2022, retrieved on Feb. 8, 2023, retrieved from URL<http://primo.ai/index.php?title=Processing_Units_-CPU,_GPU,_APU,_TPU,_VPU,_FPGA,_QPU>, 20 pages.
Principles of Neurodynamics, Perceptrons and the Theory of Brain Mechanisms, Cornell Aeronautical Laboratory, Inc F., Rosenblatt, Mar. 15, 1961, 626 pages.
Roths et al., "Strain calibration of optical FBG-based strain sensors," Proc. SPIE 7653, Fourth European Workshop on Optical Fibre Sensors, Sep. 8, 2010, 4 pages (abstract only).
Rumelhart et al., "Learning representations by back-propagating errors," Nature, Oct. 1, 1986, 4 pages.
Schmidhuber, "Deep learning in neural networks: An overview," CoRR, Submitted on Apr. 30, 2014, arXiv:1404.7828, 88 pages.
Tan et al., "A Survey on Deep Transfer Learning," CoRR, submitted on Aug. 6, 2018, arXiv:1808.01974, 10 pages.
Tan et al., "High-precision calibration method for fiber Bragg grating strain sensing based on an optical lever," Optical Fiber Technology, Jan. 2021, 61:2021 (abstract only).
Towardsdatascience.com [online], "Machine Learning and Signal Processing," Aug. 9, 2020, retrieved on Feb. 8, 2023, retrieved from URL<https://towardsdatascience.com/machine-learning-and-signal-processing-103281d27c4b>, 27 pages.
Weiss et al., "A survey of transfer learning," J Big Data, May 28, 2016, 3(9):1-40.
Wikipedia.org [online], "Group method of data handling," Nov. 25, 2022, retrieved on Feb. 8, 2023, retrieved from URL<https://en.wikipedia.org/wiki/Group_method_of_data_handling>, 6 pages.
Wikipedia.org [online], "Universal approximation theorem," Feb. 5, 2023, retrieved on Feb. 8, 2023, retrieved from URL<https://en.wikipedia.org/wiki/Universal_approximation_theorem>, 9 pages.
Xu et al., "Curvature, Torsion, and Force Sensing in Continuum Robots Using Helically Wrapped FBG Sensors," IEEE robotics & automation letters, Feb. 17, 2016, 1(2):1052-1059.
Yuksel et al., "Optical Frequency Domain Reflectometry: A Review," 11th International Conference on Transparent Optical Networks, Jun. 2009, 5 pages.

* cited by examiner

OPTICAL FIBER SHAPE SENSING

CLAIM OF PRIORITY

This application claims priority under 35 USC § 119(e) to U.S. Patent Application Ser. No. 63/423,755, filed on Nov. 8, 2022, the entire contents of which are hereby incorporated by reference.

TECHNICAL FIELD

This disclosure relates to sensing a shape of an optical fiber.

BACKGROUND

Electromagnetic Tracking (EMT) systems are used to aid in locating instruments and patient anatomy in medical procedures. These systems utilize a magnetic transmitter in proximity to one or more magnetic sensors. The one or more sensors can be spatially located relative to the transmitter and sense magnetic fields produced by the transmitter.

SUMMARY

Some tracking systems include an optical fiber to provide pose information (i.e., position and orientation) in medical procedures and are used to locate instruments and make measurements with respect to patient anatomy. These medical procedures span many domains and can include: surgical interventions, diagnostic procedures, imaging procedures, radiation treatment, etc. An optical fiber can be attached to an instrument in a medical procedure in order to provide pose information (i.e., position and orientation) for the instrument. While many methodologies may be employed to provide pose information about the optical fiber, artificial intelligence techniques, such as machine learning, can exploit measured strain data and pose information for training and evaluation. By developing such techniques to determine shape and pose information, applications and computations for tracking an instrument in a medical procedure can be improved.

In an aspect, a computing device implemented method includes receiving data representing strains experienced at multiple positions along a fiber, the fiber being positioned within a surgical theater, determining a shape of the fiber from the received data representing the stains experienced at the multiple positions along the fiber by using a machine learning system, the machine learning system being trained using data representing shapes of fibers and data representing strains at multiple positions along each of the fibers, and representing the determined shape as functions of an orientation of a center of the fiber, a first radial axis of the fiber, and a second radial axis of the fiber.

Implementations may include one or more of the following features. The data may include a magnitude and phase shift of reflected light along the fiber. Receiving data may include receiving two different polarizations of reflected light. The fiber may be one of a plurality of fibers within a multiple optical fiber sensor, and the method may include determining an overall shape of the multiple optical fiber sensor. The fiber may include one or more Fiber Bragg Gratings to provide return signals that represent the strain. The method may include receiving data from a reference path that is fixed in a reference shape. The data representing strains may include interference patterns between light reflected from the reference path and light reflected from the fiber. The multiple positions may be equally spaced along the fiber. The training data may include simulated data. The training data may include simulated data and physical data collected from one or more optical fibers.

In another aspect, a system includes a computing device that includes a memory configured to store instructions. The system also includes a processor to execute the instructions to perform operations that include receiving data representing strains experienced at multiple positions along a fiber, the fiber being positioned within a surgical theater, determining a shape of the fiber from the received data representing the stains experienced at the multiple positions along the fiber by using a machine learning system, the machine learning system being trained using data representing shapes of fibers and data representing strains at multiple positions along each of the fibers, and representing the determined shape as functions of an orientation of a center of the fiber, a first radial axis of the fiber, and a second radial axis of the fiber.

Implementations may include one or more of the following features. The data may include a magnitude and phase shift of reflected light along the fiber. Receiving data may include receiving two different polarizations of reflected light. The fiber may be one of a plurality of fibers within a multiple optical fiber sensor, and the operations may include determining an overall shape of the multiple optical fiber sensor. The fiber may include one or more Fiber Bragg Gratings to provide return signals that represent the strain. The operations may include receiving data from a reference path that is fixed in a reference shape. The data representing strains may include interference patterns between light reflected from the reference path and light reflected from the fiber. The multiple positions may be equally spaced along the fiber. The training data may include simulated data. The training data may include simulated data and physical data collected from one or more optical fibers.

In another aspect, one or more computer readable media storing instructions are executable by a processing device, and upon such execution cause the processing device to perform operations that include receiving data representing strains experienced at multiple positions along a fiber, the fiber being positioned within a surgical theater, determining a shape of the fiber from the received data representing the stains experienced at the multiple positions along the fiber by using a machine learning system, the machine learning system being trained using data representing shapes of fibers and data representing strains at multiple positions along each of the fibers, and representing the determined shape as functions of an orientation of a center of the fiber, a first radial axis of the fiber, and a second radial axis of the fiber.

Implementations may include one or more of the following features. The data may include a magnitude and phase shift of reflected light along the fiber. Receiving data may include receiving two different polarizations of reflected light. The fiber may be one of a plurality of fibers within a multiple optical fiber sensor, and the operations may include determining an overall shape of the multiple optical fiber sensor. The fiber may include one or more Fiber Bragg Gratings to provide return signals that represent the strain. The operations may include receiving data from a reference path that is fixed in a reference shape. The data representing strains may include interference patterns between light reflected from the reference path and light reflected from the fiber. The multiple positions may be equally spaced along the fiber. The training data may include simulated data. The training data may include simulated data and physical data collected from one or more optical fibers.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

Like reference numbers and designations in the various drawings indicate like elements.

DETAILED DESCRIPTION

Tracking systems such as Six Degree of Freedom (6DOF) Tracking Systems (e.g., tracking systems that employ 6DOF sensors) can be used in medical applications (e.g., tracking medical equipment in surgical theaters) to track one or more objects (e.g., a medical device such as a scalpel, one or more robotic arms, etc.), thereby determining and identifying the respective three-dimensional location, orientation, etc. of the object or objects for medical professionals (e.g., a surgeon). Such tracking can be employed for various applications such as providing guidance to professionals (e.g., in image-guided procedures), and in some cases may reduce reliance on other imaging modalities, such as fluoroscopy, which can expose patients to ionizing radiation that can potentially create health risks.

In some implementations, the 6DOF Tracking System can be realized as an electromagnetic tracking system, an optical tracking system, etc. and can employ both electromagnetic and optical components. For example, a 6DOF tracking systems can employ active electromagnetic tracking functionality and include a transmitter (or multiple transmitters) having one or more coils configured to generate one or more electromagnetic fields such as an alternating current (AC) electromagnetic (EM) field. A sensor having one or more coils located in the general proximity to the generated EM field can measure characteristics of the generated EM field and produce signals that reflect the measured characteristics. The measured characteristics of the EM field depend upon on the position and orientation of the sensor relative to the transmitter and the generated EM field. The sensor can measure the characteristics of the EM field and provide measurement information to a computing device such as a computer system (e.g., data representing measurement information is provided from one or more signals provided by the sensor). From the provided measurement information, the computing device can determine the position, shape, orientation, etc. of the sensor. Using this technique, the position, orientation, etc. of a medical device (e.g., containing the sensor, attached to the sensor, etc.) can be determined and processed by the computing device (e.g., the computing device identifies the position and location of a medical device and graphically represents the medical device, the sensor, etc. in images such as registered medical images, etc.).

Figure 1:
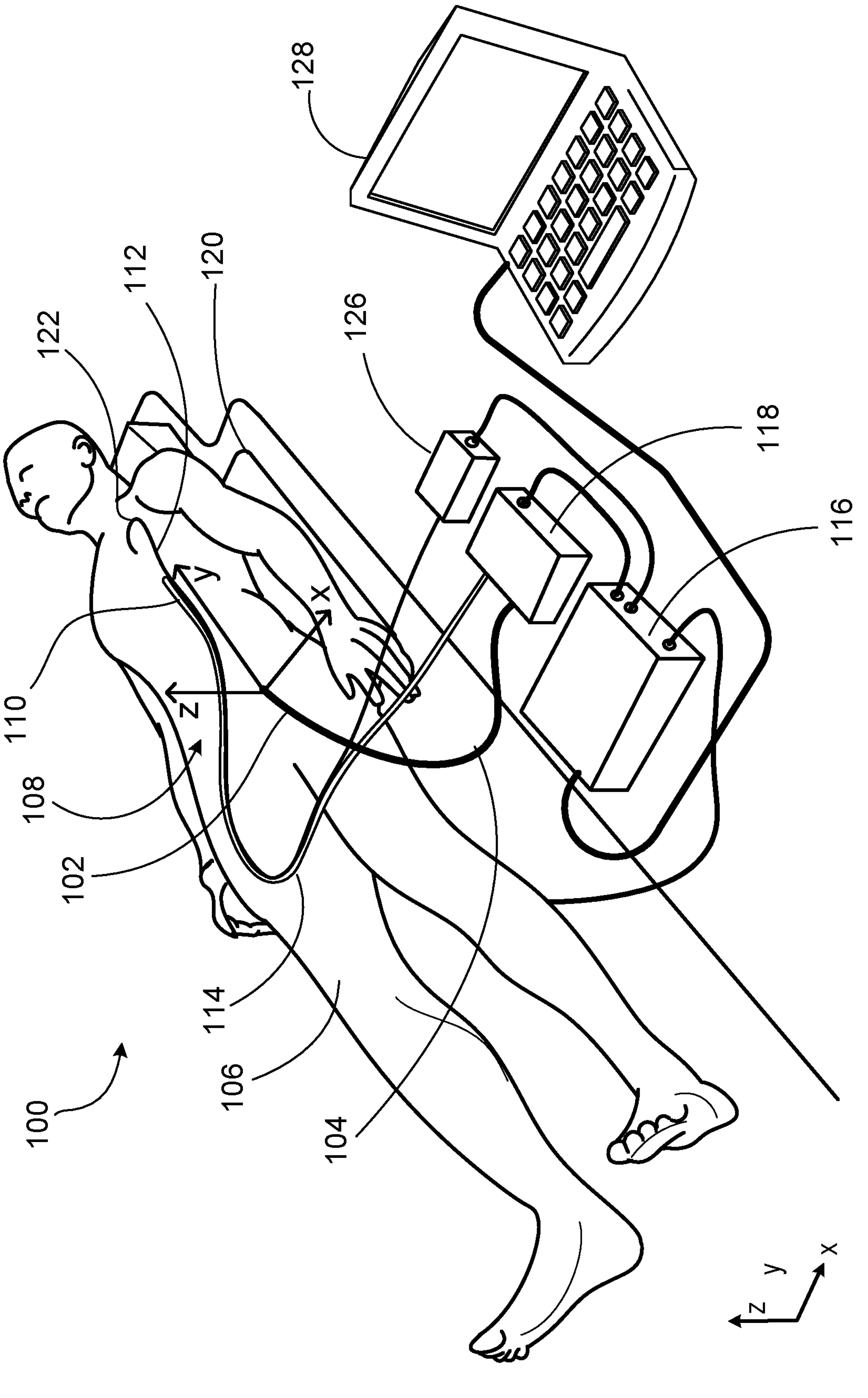
FIG. 1 is a schematic diagram of an example Electromagnetic Tracking (EMT) system.

FIG. 1 shows an example of an electromagnetic tracking (EMT) system 100 that is implemented in the surgical environment (e.g., a surgical theater). By collecting information, the system 100 can determine the location of one or more electromagnetic sensors associated with medical devices (e.g., scalpels, probes, guidewires, etc.), equipment, etc. One or more sensors can be embedded in a guidewire for tracking the guidewire in various medical procedures involving a patient. Tracking the guidewire can be useful to determine the position of the guidewire within the patient (e.g., the patient's vasculature). Once the shape and position of the guidewire is determined, the guidewire can be used to guide other medical instruments (e.g., catheters) through the patient (e.g., the patient's vasculature). The electromagnetic tracking techniques employed for tracking guidewires, for example, may be similar to those described in U.S. patent application Ser. No. 13/683,703, entitled "Tracking a Guidewire", filed on Nov. 21, 2012, which is hereby incorporated by reference in its entirety.

In the illustrated example, an electromagnetic tracking system 100 includes an electromagnetic sensor 102 (e.g., a 6DOF sensor) or multiple sensors embedded in a segment (e.g., leading segment) of a wire 104 that is contacting a patient 106. In some arrangements, a sensor (e.g., a 6DOF sensor) or sensors can be positioned in one or more different positions along the length of the wire 104. For example, multiple sensors can be distributed along the length of the wire 104.

To produce understandable tracking data, a reference coordinate system is established by the tracking system 100. The relative pose (e.g., location, position) of sensors can be determined relative to the reference coordinate system. The electromagnetic sensor 102 can be attached to the patient 106 and used to define a reference coordinate system 108. Pose information (e.g., location coordinates, orientation data, etc.) about additional sensors, can be determined relative to this reference coordinate system. The electromagnetic sensor 106 can define the reference coordinate system 108 relative to the patient because the electromagnetic sensor 102 is attached to the patient. In some implementations (e.g., implementations that include multiple sensors), by establishing the reference coordinate system 108 and using electromagnetic tracking, a location and orientation of another electromagnetic sensor 110 (e.g., a second 6DOF sensor) or multiple sensors embedded in a leading segment of a guidewire 112 can be determined relative to the reference coordinate system 108. Defining one reference coordinate system allows data to be viewed from one frame of reference, for example location data associated with a sensor, location data associated with the patient, etc. are all placed on the same frame of reference so the data is more easily understandable. In some implementations, a catheter 114 is inserted over the guidewire after the guidewire is inserted into the patient.

In this particular implementation, a control unit 116 and a sensor interface unit 118 are configured to resolve signals produced by the sensors. For example, the control unit 116 and the sensor interface 118 can receive the signals produced by the sensors (e.g., through a wired connection, wirelessly, etc.). The control unit 116 and the sensor interface 118 can determine the pose of the sensors 106, 110 using electromagnetic tracking methodologies. The pose of the sensor 106 defines the reference coordinate system 108, as discussed above. The pose of the sensor 110 provides information about the leading segment of the guidewire 112. Similar to electromagnetic systems, optical based systems may employ techniques for tracking and identifying the respective three-dimensional location, orientation, etc. of objects for medical professionals. Or, in the case where the Tracking System 100 employs optical tracking capabilities, the pose of the sensors 106, 110 can be determined using optical tracking methodologies.

The geometry and dimensions of the guidewire can vary. In some implementations, the guidewire 112 may have a maximum diameter of about 0.8 mm. In some implementation, the guidewire 112 may have a diameter larger or smaller than about 0.8 mm. The guidewire can be used to guide medical equipment or measurement equipment through the patient (e.g., through the patient's vasculature). For example, the guidewire may guide optical fibers through the patient. While the guidewire 112 may have a cylindrical geometry, one or more other types of geometries may be employed (e.g., geometries with rectangular cross sections). In some implementations, a guidewire may include a bundle of wires.

A field generator 120 resides beneath the patient (e.g., located under a surface that the patient is positioned on, embedded in a surface that the patient lays upon—such as a tabletop, etc.) to emit electromagnetic fields that are sensed by the accompanying electromagnetic sensors 102, 110. In some implementations, the field generator 120 is an NDI Aurora Tabletop Field Generator (TTFG), although other field generator techniques and/or designs can be employed.

The pose (i.e., the position and/or orientation) of a tracked sensor (e.g., the first tracking sensor 102, the second tracking sensor 110) refers to a direction the tracked sensor is facing with respect to a global reference point (e.g., the reference coordinate system 108), and can be expressed similarly by using a coordinate system and represented, for example, as a vector of orientation coordinates (e.g., azimuth ($\psi$), altitude ($\theta$), and roll ($\varphi$) angles) or Cartesian coordinates (e.g., x, y, and z). The tracking system 100 operates to determine a shape of an optical fiber, as discussed below. Additionally, the tracking system 100 operates to be an up to six degree of freedom (6DOF) measurement system that is configured to allow for measurement of position and orientation information of a tracked sensor related to a forward/back position, up/down position, left/right position, azimuth, altitude, and roll. For example, if the second tracking sensor 110 includes a single receiving coil, a minimum of at least five transmitter assemblies can provide five degrees of freedom (e.g., without roll). In an example, if the second tracking sensor 110 includes at least two receiving coils, a minimum of at least six transmitter assemblies can provide enough data for all six degrees of freedom to be determined. Additional transmitter assemblies or receiving coils can be added to increase tracking accuracy or allow for larger tracking volumes.

The guidewire 112 can be instrumented by (e.g., affixed to, encapsulating, etc.) an optical fiber (not shown). The optical fiber can form one or multiple shapes as it extends into and through the body of the patient. Light that is transmitted down the fiber can be used to track the location, orientation, (i.e., pose) of segments of the fiber, and as an outcome fiber shape information can be determined. In the example shown in FIG. 1, a hook shape 122 is produced by the guidewire 112, which can be resolved by the system 100. A starting location of a segment of the fiber is known by the system 100 due to the pose of the second electromagnetic sensor 110 being known. The fiber can be tracked relative to the second electromagnetic sensor 110 based on a fiber optic signal. For example, an interrogator 126 receives fiber optic signals (e.g., a waveform that is reflected back) reflected through the optical fiber. The received fiber optic signals can be used to determine the mechanical strain along the length of the fiber, and therefore also its shape. For example, the shape of the segment of fiber may be determined based on the fiber optic signals transmitted to and from the interrogator 126.

In some implementations, fiber optic tracking may be limited to local tracking. A reference coordinate system is provided by the first electromagnetic sensor 102. The location and orientation of the second electromagnetic sensor 110 is known due to electromagnetic tracking. Thus, only the segment of fiber that extends beyond the second electromagnetic sensor 110 must be tracked. For example, the control unit 116 and sensor interface unit 118 can resolve sensor signals to determine the pose of the sensors 102, 110 using electromagnetic tracking methodologies, discussed further below. Shape information from the optical fiber can then be fused with the pose information of electromagnetic sensors 110 and 102 on a computer system 128 and can be computed in the patient reference frame (e.g., in the reference coordinate system 108). In doing so, the shape information can be further processed for visualization with other data that is registered to the patient reference, for example manually created annotations or medical images collected prior to or during the procedure.

In some implementations, the interrogator 126 is an optoelectronic data acquisition system that provides measurements of the light reflected through the optical fiber. The interrogator provides these measurements to the computing device (e.g., the computer system 128).

At each periodic refraction change due to the shape of the optical fiber, a small amount of light is reflected. The reflected light signals combine coherently to produce a relatively large reflection at a particular wavelength (e.g., when the grating period is approximately half the input light's wavelength). For example, reflection points can be set up along the optical fiber, e.g., at points corresponding to half wavelengths of the input light. This is referred to as the Bragg condition, and the wavelength at which this reflection occurs is called the Bragg wavelength. Light signals at wavelengths other than the Bragg wavelength, which are not phase matched, are essentially transparent. In general, a fiber Bragg grating (FBG) is a type of distributed Bragg reflector constructed in a relative short segment of optical fiber that reflects particular wavelengths of light and transmits the light of other wavelengths. An FBG can be produced by creating a periodic variation in the refractive index of a fiber core, which produces a wavelength-specific dielectric mirror. By employing this technique, a FBG can be used as an inline optical fiber for sensing applications.

Therefore, light propagates through the grating with negligible attenuation or signal variation. Only those wavelengths that satisfy the Bragg condition are affected and strongly back-reflected. The ability to accurately preset and maintain the grating wavelength is one main feature and advantage of Fiber Bragg gratings.

The central wavelength of the reflected component satisfies the Bragg relation: $\lambda_{Bragg}=2\ n\Lambda$, with n being the index of refraction and $\Lambda$ being the period of the index of refraction variation of the FBG. Due to the temperature and strain dependence of the parameters n and $\Lambda$, the wavelength of the reflected component will also change as function of temperature and/or strain. This dependency can be utilized for determining the temperature or strain from the reflected FBG wavelength.

In some implementations, the sensor 102 provides a reference coordinate system 108 for the system 100 that may be aligned to the patient 106. The location, orientation, shape, etc. of the guidewire 112 can be defined within the reference coordinate system. In this way, the fiber can be tracked relative to the patient anatomy. In some implementations, the guidewire 112 may include NDI Aurora magnetic sensors or be tracked by NDI's optical tracking systems.

In some cardiac applications the shape of the segment of optical fiber can be used to support medical procedures. For example, the shape of the segment of optical fiber can provide information about a transeptal puncture operation in the context of a mitral valve repair/replacement or a catheter across an atrial septum wall for atrial fibrillation treatment. Additionally, the shape of the segment of fiber can be used to cannulate the vessel entering the kidney from the aorta for a stent placement.

Tracking systems are frequently accompanied by computing equipment, such as the computer system 128, which can process and present the measurement data. For example, in a surgical intervention, a surgical tool measured by the tracking system can be visualized with respect to the anatomy marked up with annotations from the pre-operative plan. Another such example may include an X-ray image annotated with live updates from a tracked guidewire.

Medical procedures that are supported by tracking systems frequently make measurements with respect to a reference co-ordinate system located on the patient. In doing so, medical professionals can visualize and make measurements with respect to the patient anatomy and correct for gross patient movement or motion. In practice, this is accomplished by affixing an additional electromagnetic sensor (e.g., a 6DOF sensor) to the patient. This is also accomplished by sensing the shape of the guidewire 112.

The described tracking systems can be advantageous because they do not require line-of-sight to the objects that are being tracked. That is, they do not require a directly unobstructed line between tracked tools and a camera for light to pass. In some implementations, the described systems have improved metal immunity and immunity to electrical interference. That is, they do not require minimal presence of metals and sources of electrical noise in their vicinity to provide consistent tracking performance.

In medical procedure contexts where the approach of a surgical or endoscopic tool can improve patient outcomes, additional intraoperative imaging modalities can be used such as Ultrasound, MRI, or X-rays. Another advantage of the described tracking systems (e.g., the system 100 of FIG. 1) is that the shape of the surgical/endoscopic tool is not distorted by imaging artifacts. Also, EMT systems do not require direct manual control of an imaging probe by a skilled practitioner to maintain the quality of visualization. Also, the present systems do not expose the patient and medical staff to ionizing radiation. Thus the number of workflow contexts that stand to benefit from this technology is vast, covering a variety of endovascular procedures, electrophysiology, structural heart interventions, peripheral vascular interventions, bronchoscopic interventions, endoscopic procedures, neurosurgical interventions, biopsy needle guidance, percutaneous coronary interventions, transcatheter embolization procedures, pain management procedures, urological interventions, robotic laparoscopic interventions, and others.

There are techniques by which optical transducers built into an optical fiber can produce measurements (for example wavelength) that can be used to estimate pose information along the length of the fiber. In some implementations, the optical fiber may be equipped with a series of FBGs, which amount to a periodic change in the refractive index manufactured into the optical fiber. In some implementations, the optical fiber may rely on Rayleigh scattering, which is a natural process arising from microscopic imperfections in the fiber. Techniques using FBG, Rayleigh scattering, both, etc. have the capacity to reflect specific wavelengths of light that may correspond to strain or changes in temperature within the fiber. Deformations in the fiber cause these wavelengths to shift, and the wavelength shift can be measured by a system component referred to as an interrogator 126 that measures wavelength shift by using Wavelength-Division Multiplexing (WDM), Optical Frequency-Domain Reflectometry (OFDR), etc. In doing so, the shape of the fiber can be estimated, for example, by employing one or more artificial intelligence techniques such as a trained machine learning system. By affixing a fiber instrumented as such, a sensing/measurement paradigm can be realized for 6DOF tracking systems, enabling the pose and shape measurements along the fiber in the co-ordinate space of the 6DOF tracking system. Additionally, in an optical tracking supported procedure, this can allow one to take pose measurements outside of the measurement volume or line-of-sight of the optical tracking system. In the context of an electromagnetic tracking supported procedure, this can allow one to take pose measurements in a region with high metal distortion where electromagnetic sensors would normally perform poorly, or one can use the fiber measurements to correct for electromagnetic/metal distortion.

While FIG. 1 is largely directed to a system 100 that includes electromagnetic components (e.g., an electromagnetic tracking system), it should be understood that the one or more sensors (e.g., 6DOF sensors) described herein may be part of other (e.g., different) systems, such as optical tracking systems that include one or more cameras and one or more sensors (e.g., 6DOF sensors).

As described above, the operation of the system 100 can be controlled by a computer system 128. In particular, the computer system 128 can be used to interface with the system 100 and cause the locations/orientations of the electromagnetic sensors 102, 110 and the segment of fiber within the guidewire 112 to be determined.

Figure 2:
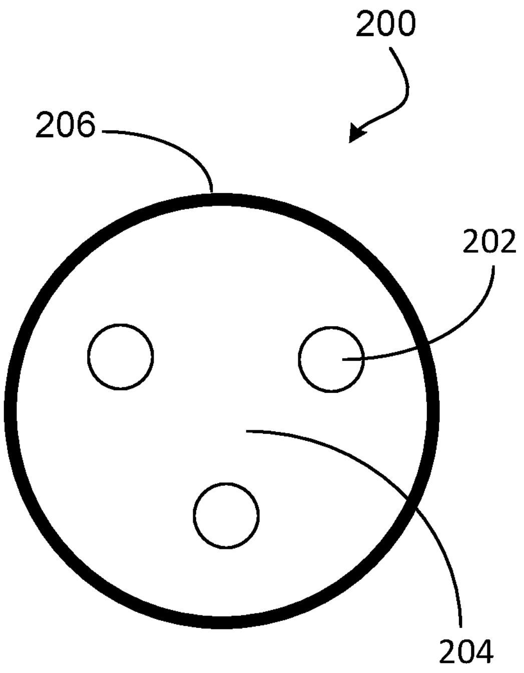
FIG. 2 illustrates a cross section of an optical fiber.

The segment of fiber within the guidewire 112 can include multiple components, structures, etc. FIG. 2 shows an exemplary cross section of a multiple optical fiber sensor (MFOS) 200. The MFOS 200 can be, e.g., a multi-core fiber optic sensor or multiple, mechanically bundled fiber optic sensors. For example, three cores 202 can perform 3D shape sensing. Lesser degrees of freedom can be realized with fewer fibers. MFOS 200 consists of multiple optical cores 202, surrounded by cladding 204, with a coating 206 for protection.

The cores 202 are the physical medium of the fiber that carries the light signal received from an attached light source and delivers it to a receiving device. For example, the cores 202 can be continuous hair-thin strands of silica glass or plastic. The cladding 204 is a thin layer of glass that surrounds the fiber cores 202, forming a single solid glass fiber that is used for light transmission. The cladding 204 creates a boundary containing the light waves and causing refraction, which enables data to travel the length of the fiber. The coating 206 is designed to absorb shocks, provide protection against excessive cable bends, and reinforce the fiber cores 202. The coating 206 can be a layer of plastic which does not interfere with the cladding 204 or the light transmission of the cores 202.

Figure 3:
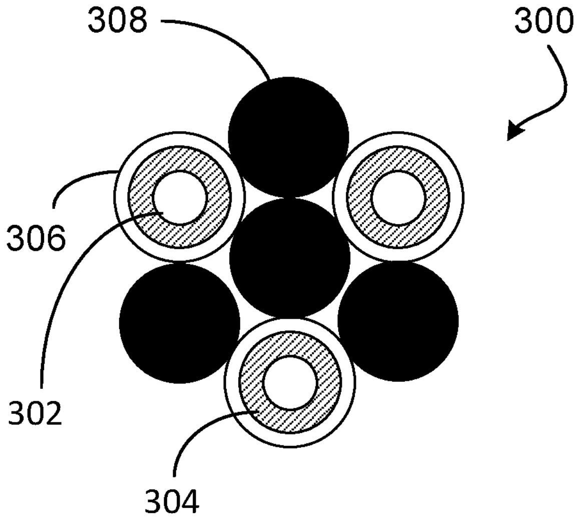
FIG. 3 illustrates a cross section of another optical fiber.

Optical fibers can include more or fewer components than those shown in FIG. 2. For example, FIG. 3 is an exemplary cross section of a MFOS 300 that can be, e.g., a multi-core fiber optic sensor or multiple, mechanically bundled fiber optic sensors. For example, three cores 302 can perform 3D shape sensing. Lesser degrees of freedom can be realized with fewer fibers. MFOS 300 consists of multiple optical cores 302, surrounded by cladding 304, with a coating 306 for protection. The MFOS 300 includes additional strength/positioning elements 308. These elements 308 keep the sensing fibers in a certain geometry and provide additional support to the fibers. The sensor 300 may be further encased in epoxy for strength. For example, the sensor 300 can be twisted during epoxy bonding resulting in a helical structure. The overall diameter of the MFOS 200 shown in FIG. 2 can be much smaller than the MFOS 300 of FIG. 3.

Figure 5:
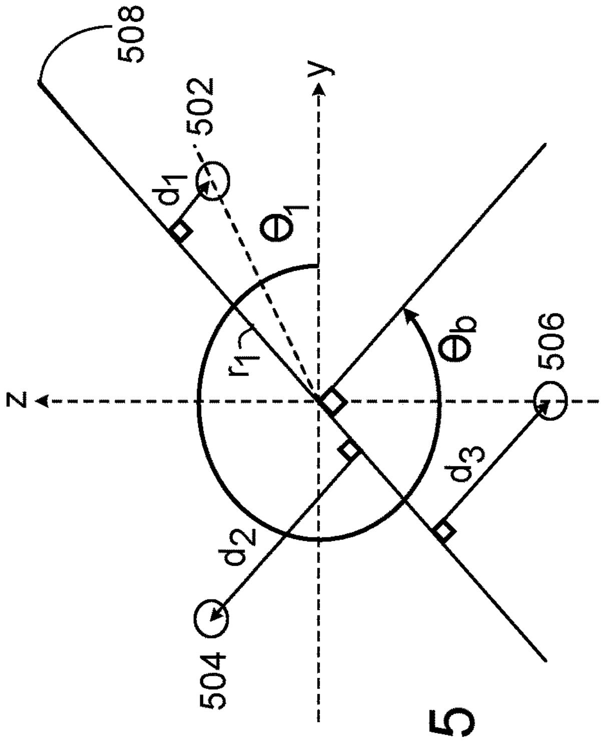
FIG. 5 illustrates another convention for representing a shape of an optical fiber.
Figure 4:
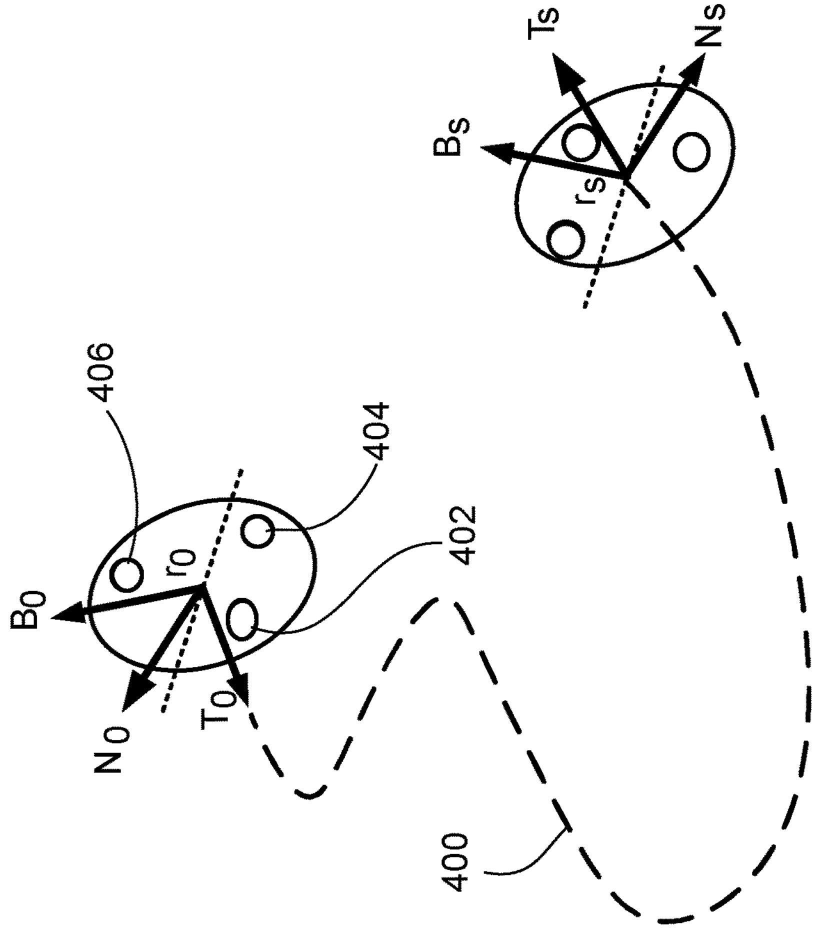
FIG. 4 illustrates a convention for representing a shape of an optical fiber.

Pose information (e.g., position, orientation, shape) of an optical fiber can be defined, e.g., by a number of functions. FIGS. 4 and 5 illustrate a randomly simulated shape 400 of an MFOS. The random 3-D shape is generated as a function of x(s), y(s) and z(s), which together represent the overall shape 400 (e.g., shape(s)) of the MFOS. The simulated shape may have constraints such that the shape represents typical usage scenarios, lengths, tortuosity, etc. When simulating the shape 400, initial conditions (e.g., initial location, orientation, etc.) can be set. In the illustrated example, the initial conditions are the initial location and orientation of a first end of the MFOS. Once the shape is fully simulated, T(s), N(s) and B(s) are calculated at discrete points s throughout the shape 400. T(s) defines the orientation of the center of the MFOS at each point s. N(s) defines a radial axis of the MFOS, perpendicular to T(s) at each point s. B(s) defines another radial axis of the MFOS, perpendicular to T(s) and N(s) at each point s. T(s), N(s) and B(s) define the area of the MFOS at each point s along the shape 400. The number of discrete points s throughout the shape 400 can vary based on requirements for smoothness and are not necessarily equally spaced. Additional fiber cores in the MFOS are simulated about the curve of the shape 400. In the illustrated implementation, there are three cores 402, 404, 406. In other implementations, there can be more or fewer fiber cores. In some implementations, there can be a core at the center of the shape 400.

The simulation of the additional cores is performed by forming a curve for the core as a function of s and t, where s parametrizes the length of the core and t parameterizes the orientation of the core. Each additional core has a respective curve. For example, with three cores 402, 404, 406, there are three additional curves. Assuming the cores are evenly spaced around a circle of radius r, where r, is the radial distance of each core from the center of the shape, the location of each core relative to the center of the shape 400 can be determined from equation (1). In this example, t could be three values to evenly space the cores (e.g., 0, 2π/3, 4π/3). As discussed above, the shape 400 is comprised of three components, x(s), y(s) and z(s) and there are also three components each of T(s), N(s), and B(s).

$$\text{Curve}(s,t)=\text{shape}(s)+N(s)r\cos(t)+B(s)r\sin(t) \quad (1)$$

With the cores simulated about the center of the shape 400, the angles and distances of the cores relative to the center of the shape 400 can be determined at each point s along the shape 400. With additional reference to FIG. 5, the angle $\Theta_1$ and distances $r_1$ and $d_1$ can be calculated for the angle and distance of the first core 502 from the center of the MFOS. The angle $\Theta_1$ and radius $r_1$ can act as polar coordinates to define the position of the core relative to the center of the MFOS. The bend axis angle $\Theta_b$ can define the direction of a bend in the MFOS. A bend axis 508 is perpendicular from the bend axis angle $\Theta_b$. The distance $d_1$ defines the distance of the first core 502 from the bend axis angle 508.

Once the angle and distance of each core relative to the shape 400 is determined, e.g., at each point s along the shape 400, the curvature κ of each individual cores 402, 404, 406 can be determined at each point s along the shape 400. The curvature K is determined by calculating for each core curve.

$$\kappa_i(s)=\|T'_i(s)\| \quad (2)$$

Once information regarding κ and d is determined, e.g., relative to the shape 400, the strain ε, e.g., due to twisting and bending, on each core can be determined.

Figure 6:
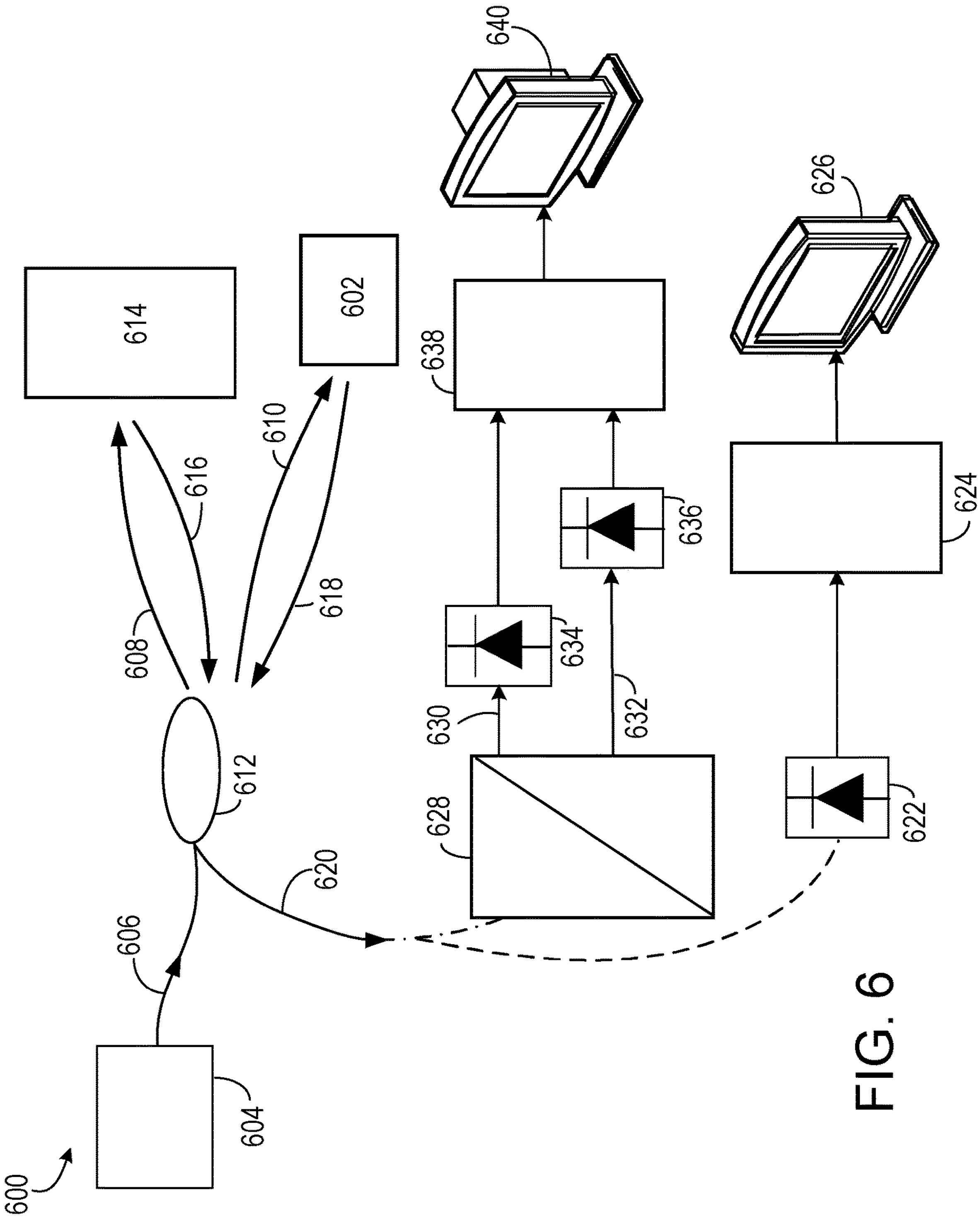
FIG. 6 shows a data flow diagram that graphically represents collecting strain data of an optical fiber.

FIG. 6 illustrates a block diagram for collecting strain data in an optical fiber graphically represents a Fiber Optic Shape Sensing (FOSS) system 600 that utilizes Optical Frequency Domain Reflectometry (OFDR) and an MFOS 602. A tunable laser source 604 is linearly swept over a limited range of wavelengths, e.g., about 1-1.5 μm. A light 606 emitted by the laser source 604 is divided into two beams 608 and 610 by optical coupler 612. The beam 608 follows a reference light path 614 and is fixed by design. The reference path 614 receives beam 608 and returns beam 616. The second beam 610 is sent into the MFOS 602 and the MFOS returns beam 618, which carries information related to the strain in the MFOS 602. The returning beams 616 and 618 cause interference patterns to occur in coupler 612. These interference patterns are represented in a beam 620.

The beam 620 containing the interference patterns can be analyzed through a variety of methods. For example, the beam 620 can be analyzed for amplitude information, which is not phase-sensitive. In this case, the interference represented in the beam 620 is measured by a photodetector 622. The photodetector 622 converts light into electrical signals that are then processed by a data acquisition system 624. The data acquisition system 624 can include, e.g., one or more analog to digital (A/D) converters. One or more other signal processing techniques may also be employed in the data acquisition system 624 (e.g., filtering, etc.). The data processed by the data acquisition system 624 can be provided (e.g., uploaded) to a computer system 626. The computer system 626 can be trained by a machine learning (ML) process, where the data from the data acquisition system 624 can be converted into a shape of the MFOS 602.

Another technique of analyzing the beam 620 containing the interference patterns is analyzing both amplitude and phase information (e.g., a phase sensitive technique). For example, the beam 620 can be split into, e.g., orthogonal polarizations by a photodetector 628. For example, polarization component 630 refers to the component of the beam 620 perpendicular to the incident plane, while polarization component 632 refers to the component of the beam 620 in the plane. Each component is measured by a respective photodetectors 634, 636, which convert the respective light into electrical signals that are then processed by a data acquisition system 638. The data acquisition system 638 can include, e.g., one or more A/D converters and potentially components to perform one or more other signal processing techniques (e.g., filtering). The converted signals from the data acquisition system 638 can be provided (e.g., uploaded) to a computer system 640. The computer system 640 can be trained by a machine learning (ML) process, where the data from the data acquisition system 638 can be converted into a shape of the MFOS 602.

Figure 7:
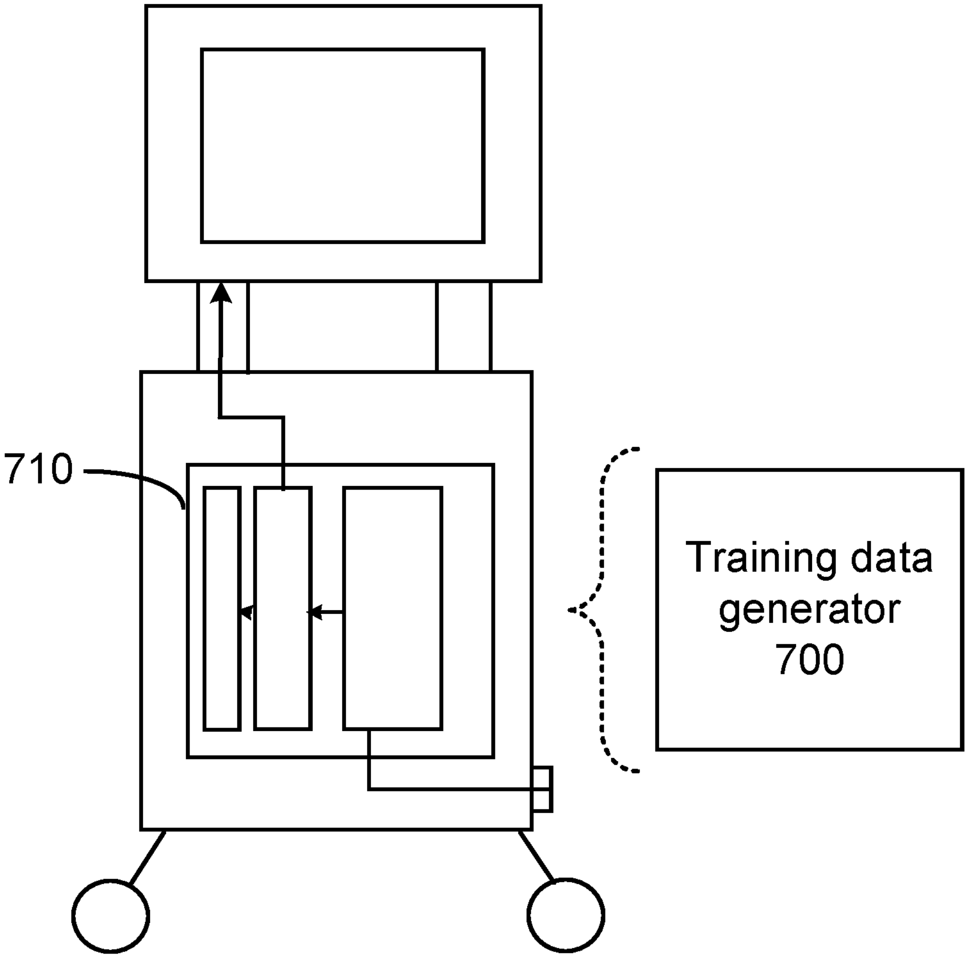
FIG. 7 is a computer system executing a training data generator that collects training data to train an optical fiber shape sensing machine learning system.

The computer systems (e.g., computer 626, 640) described can execute a training data collector, which utilizes the captured data to determine a position and orientation of a surgical tool (or other object). Referring to FIG. 7, a computer system 710 executes a training data generator 700. The computer system 710 can be similar to the computer system 128 of FIG. 1. The training data generator 700 (e.g., a program, software, software application, or code) includes machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

Figure 8:
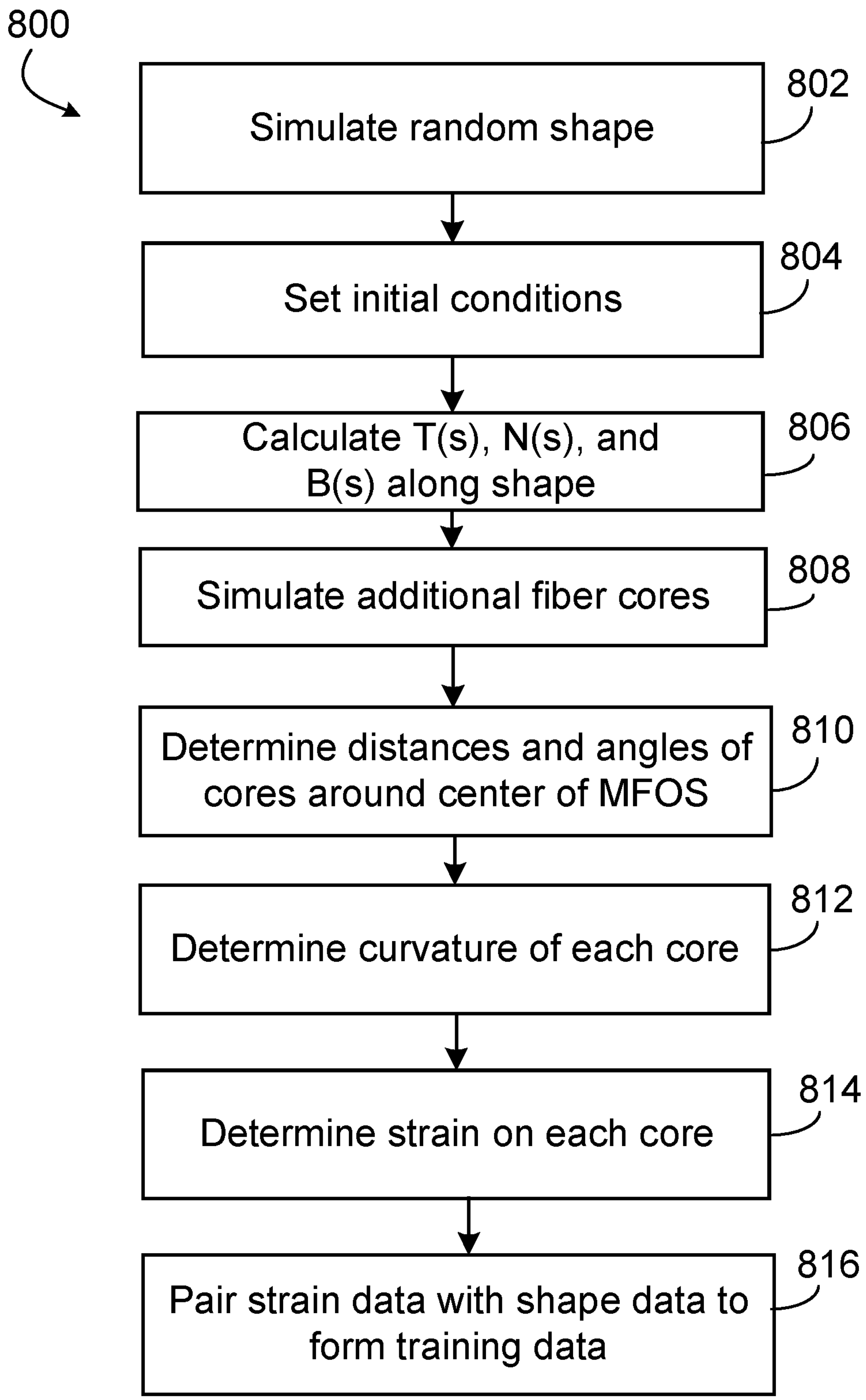
FIG. 8 is a flowchart of operations of a training data generator to computationally generate training data to train an optical fiber shape sensing machine learning system.

FIG. 8 is a flowchart 800 of a method for computationally generating data to train a machine learning system to determine a shape of an MFOS. For example, operations of a training data generator (e.g., the training data generator 700 of FIG. 7) can follow the flowchart 800. First, a random 3-D shape is simulated (802). For example, the random 3-D shape can be simulated as a function of x(s), y(s) and z(s) to represent the overall simulated shape. The simulated shape may have constraints such that the shape represents typical usage scenarios, lengths, tortuosity, etc., as described above.

Next, initial conditions for the simulated shape can be set (804). For example, the initial conditions can include an initial location and orientation of a first end of the shape. Other initial conditions can also be set (e.g., N(0), B(0)).

Then, T(s), N(s) and B(s) can calculated at discrete points s throughout the simulated shape (806). T(s) defines the orientation of the center of the shape at each point s. N(s) defines a radial axis of the shape, perpendicular to T(s) at each point s. B(s) defines another radial axis of the shape, perpendicular to T(s) and N(s) at each point s. T(s), N(s) and B(s) define the area of the shape at each point s along the simulated shape. The number of discrete points s throughout the shape can vary based on requirements for smoothness and are not necessarily equally spaced.

Next, additional fiber cores are simulated about the curve of the shape (808). For example, there can be three cores. In other implementations, there can be more or fewer fiber cores. In some implementations, there can be a core at the center of the shape. The generation of the additional cores can be performed, e.g., by forming a curve for the core as a function of s and t, where s parametrizes the length of the core and t parameterizes the orientation of the core. Each additional core can have a respective curve. For example, with three cores, there can be three additional curves. Assuming the cores are evenly spaced around a circle of radius r, where r, is the radial distance of each core from the center of the shape, the location of each core relative to the center of the shape can be determined as described above.

Then, the angles and distances of the cores relative to the center of the shape can be determined at discrete points s along the shape (810). For example, an angle Θ and distances r and d can be calculated for the angle and distance of a core from the center of the shape, as described above. The angle Θ and radius r can act as polar coordinates to define the position of the core relative to the center of the shape. A bend axis angle $\Theta_b$ can define the direction of a bend in the shape at point s.

Next, the curvature κ of each individual cores can be determined (812). For example, the curvature of each individual core can be determined for each point s along the shape, as described above.

Then, the strain ε on each core can be determined (814). For example, the strain can be due to twisting and bending. The strain P can be determined at each point s along the shape. The strain data can be represented as, e.g., vectors or matrices.

The strain ε on each core and the randomly simulated shape can then be used as ML training data. For example, the random shape and the strain data can be paired (816), and the ML training data can be used to train a machine learning system to determine the randomly simulated shape from the strain data. For example, the method 800 can be repeated as necessary to generate enough data to train the machine learning system. The machine learning system can be trained to receive core strains as input and output the shape of the MFOS.

To implement the machine learning system, one or more machine learning techniques may be employed. For example, supervised learning techniques may be implemented in which training is based on a desired output that is known for an input. Supervised learning can be considered an attempt to map inputs to outputs and then estimate outputs for previously unseen inputs (a newly introduced input). Unsupervised learning techniques may also be employed in which training is provided from known inputs but unknown outputs. Reinforcement learning techniques may also be used in which the system can be considered as learning from consequences of actions taken (e.g., inputs values are known and feedback provides a performance measure). In some arrangements, the implemented technique may employ two or more of these methodologies.

In some arrangements, neural network techniques may be implemented using the data representing the strain (e.g., a matrix of numerical values that represent strain values at each point s along a shape) to invoke training algorithms for automatically learning the shape and related information. Such neural networks typically employ a number of layers. Once the layers and number of units for each layer is defined, weights and thresholds of the neural network are typically set to minimize the prediction error through training of the network. Such techniques for minimizing error can be considered as fitting a model (represented by the network) to training data. By using the strain data (e.g., vectors or matrices), a function may be defined that quantifies error (e.g., a squared error function used in regression techniques). By minimizing error, a neural network may be developed that is capable of determining attributes for an input image. Other factors may also be accounted for during neutral network development. For example, a model may too closely attempt to fit data (e.g., fitting a curve to the extent that the modeling of an overall function is degraded).

Such overfitting of a neural network may occur during the model training and one or more techniques may be implements to reduce its effects.

One type of machine learning referred to as deep learning may be utilized in which a set of algorithms attempt to model high-level abstractions in data by using model architectures, with complex structures or otherwise, composed of multiple non-linear transformations. Such deep learning techniques can be considered as being based on learning representations of data. In general, deep learning techniques can be considered as using a cascade of many layers of nonlinear processing units for feature extraction and transformation. The next layer uses the output from the previous layer as input. The algorithms may be supervised, unsupervised, combinations of supervised and unsupervised, etc. The techniques are based on the learning of multiple levels of features or representations of the data (e.g., strain data). As such, multiple layers of nonlinear processing units along with supervised or unsupervised learning of representations can be employed at each layer, with the layers forming a hierarchy from low-level to high-level features. By employing such layers, a number of parameterized transformations are used as data propagates from the input layer to the output layer. In one arrangement, the machine learning system uses a fifty-layer deep neutral network architecture (e.g., a ResNet50 architecture).

The machine learning system can be, e.g., a neural network. Additionally, multiple smaller neural networks may be put together sequentially to accomplish what a single large neural network does. This allows partitioning of neural network functions along the major FOSS technology blocks, mainly strain measurement, bend and twist calculation and shape/position. For example, a neural network can act as a Fourier Transformer. In some implementations, training smaller networks may be more efficient. For example, determining regression models on smaller chunks of data may be more efficient than determining models on larger sets of data.

Figure 9:
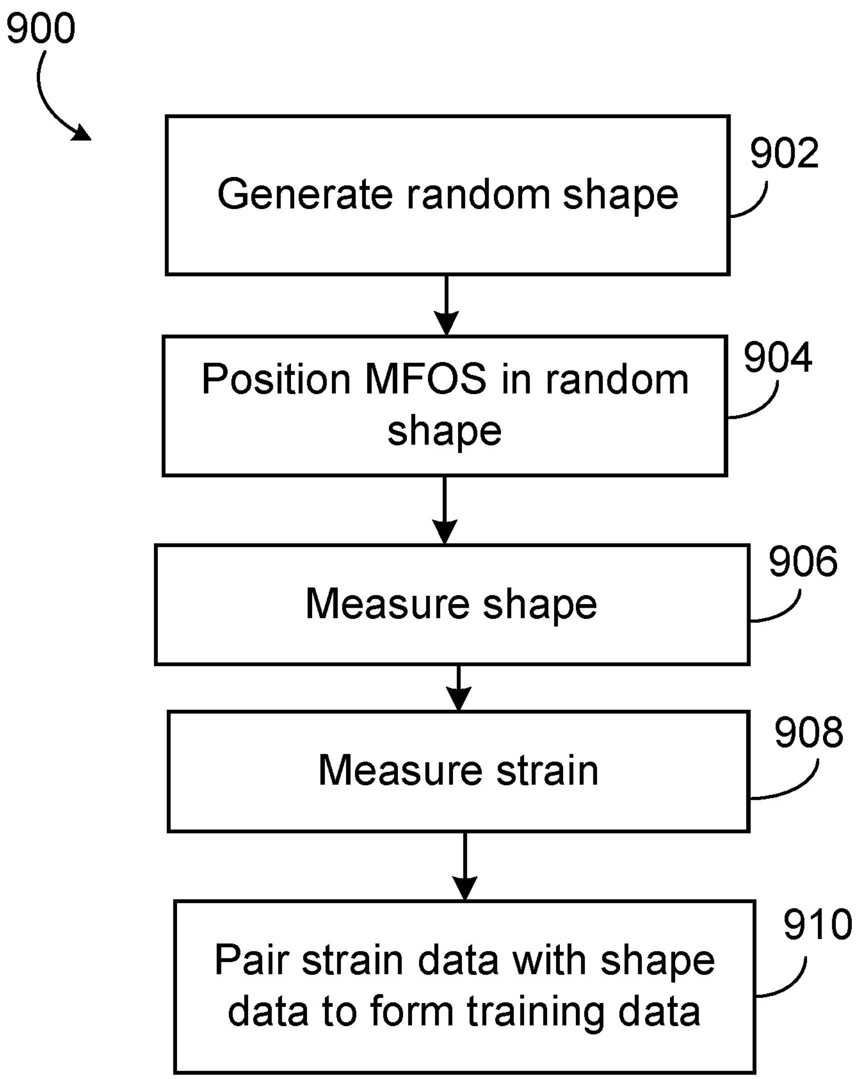
FIG. 9 is another flowchart of operations of a training data generator to physically generate training data to train an optical fiber shape sensing machine learning system.

FIG. 9 is a flowchart of a method 900 for physically generating data to train a machine learning system to determine a shape of an MFOS. For example, operations of a training data generator (e.g., the training data generator 700 of FIG. 7) can follow the method 900. In the method 900, rather than using simulated shapes, a training MFOS is set into a certain shape and the resulting strained are measured, e.g., using system 600 as described above.

First, a random shape is generated (902). For example, the random 3-D shape can be generated as a function of x(s), y(s) and z(s) to represent the overall generated shape. The generated shape may have constraints such that the shape represents typical usage scenarios, lengths, tortuosity, etc., as described above.

Next, a physical MFOS is positioned in the random generated shape (904). For example, a robotic MFOS can position itself into the random generated shape. In another example, a user can position the MFOS into the generated shape.

Then, the shape of the MFOS can be measured (906). For example, the shape of the MFOS can be measured, e.g., using a calibrating system. Measuring the shape of the MFOS using hardware equipment can improve the training data. For example, the shape of the MFOS may not be exact to the randomly simulated shape. Also, the measurements of the shape may not be exact, e.g., due to manufacturing tolerances. Along with collecting training data, the method 900 can be used to calibrate a system, e.g., similar to system 400.

Next, the strain in the MFOS can be measured (908). For example, the strain in the MFOS can be measured with a system similar to system 600. The strain P can be measured at discrete points s along the shape. The strain and the measured shape can then be used as ML training data. For example, the random shape and the strain data can be paired (910), and the ML training data can be used to train a machine learning system to determine the randomly generated shape from the strain data. The method 900 can be repeated as necessary to generate enough data to train the machine learning system. The machine learning system can be trained to receive strain data as input and output the shape of the MFOS. For example, the machine learning system can be trained similarly to the machine learning system 510, as described above.

The training data collected by the methods described above (e.g., by the training data generator 700) can be used to train a machine learning system. For example, one or more techniques may be implemented to determine shape information based on provided strains to a computer system (e.g., the computer system 126). For such techniques, information may be used from one or more data sources. For example, data (e.g., strain data) may be generated that represents the strain throughout an optical fiber. For one type of data collection method, training data can be generated using simulated shapes (e.g., similar to the method 900 of FIG. 9).

Along with the simulated shapes, other techniques may be used in concert for determining shape information. One or more forms of artificial intelligence, such as machine learning, can be employed such that a computing process or device may learn to determine shape information from training data, without being explicitly programmed for the task. Using this training data, machine learning may employ techniques such as regression to estimate shape information. To produce such estimates, one or more quantities may be defined as a measure of shape information. For example, the level of strain in two locations may be defined. One or more conventions may be utilized to define such strains. Upon being trained, a learning machine may be capable of outputting a numerical value that represents the shape between two locations. Input to the trained learning machine may take one or more forms. For example, representations of strain data may be provided to the trained learning machine. One type of representation may be phase sensitive representations of the strain data (e.g., containing both amplitude and phase information, similar to FIG. 6). Another type of representation may be non-phase sensitive representations of the strain data (e.g., containing only amplitude information). In some arrangements a machine learning system may be capable of rendering imagery from provided input. Once rendered, the imagery may be used to determine a shape of the optical fiber. The machine learning system may also be capable of rendering one or more components (e.g., x(s), y(s), and z(s)) from the provided input. Once rendered, the components can define the shape of the optical fiber, e.g., in an axis.

To implement such an environment, one or more machine learning techniques may be employed. For example, supervised learning techniques may be implemented in which training is based on a desired output that is known for an input. Supervised learning can be considered an attempt to map inputs to outputs and then estimate outputs for previously unused inputs. Unsupervised learning techniques may also be used in which training is provided from known inputs but unknown outputs. Reinforcement learning techniques may also be employed in which the system can be ,sconsidered as learning from consequences of actions taken (e.g., inputs values are known and feedback provides a performance measure). In some arrangements, the implemented technique may employ two or more of these methodologies. For example, the learning applied can be considered as not exactly supervised learning since the shape can be considered unknown prior to executing computations. While the shape is unknown, the implemented techniques can check the strain data in concert with the collected shape data (e.g., in which a simulated shape is connected to certain strain data). By using both information sources regarding shape information, reinforcement learning technique can be considered as being implemented.

In some arrangements, neural network techniques may be implemented using the training data as well as shape data (e.g., vectors of numerical values that represent shapes) to invoke training algorithms for automatically learning the shapes and related information, such as strain data. Such neural networks typically employ a number of layers. Once the layers and number of units for each layer is defined, weights and thresholds of the neural network are typically set to minimize the prediction error through training of the network. Such techniques for minimizing error can be considered as fitting a model (represented by the network) to the training data. By using the shape data and the strain data, a function may be defined that quantifies error (e.g., a squared error function used in regression techniques). By minimizing error, a neural network may be developed that is capable of estimating shape information. Other factors may also be accounted for during neutral network development. For example, a model may too closely attempt to fit data (e.g., fitting a curve to the extent that the modeling of an overall function is degraded). Such overfitting of a neural network may occur during the model training and one or more techniques may be implements to reduce its effects.

Figure 10:
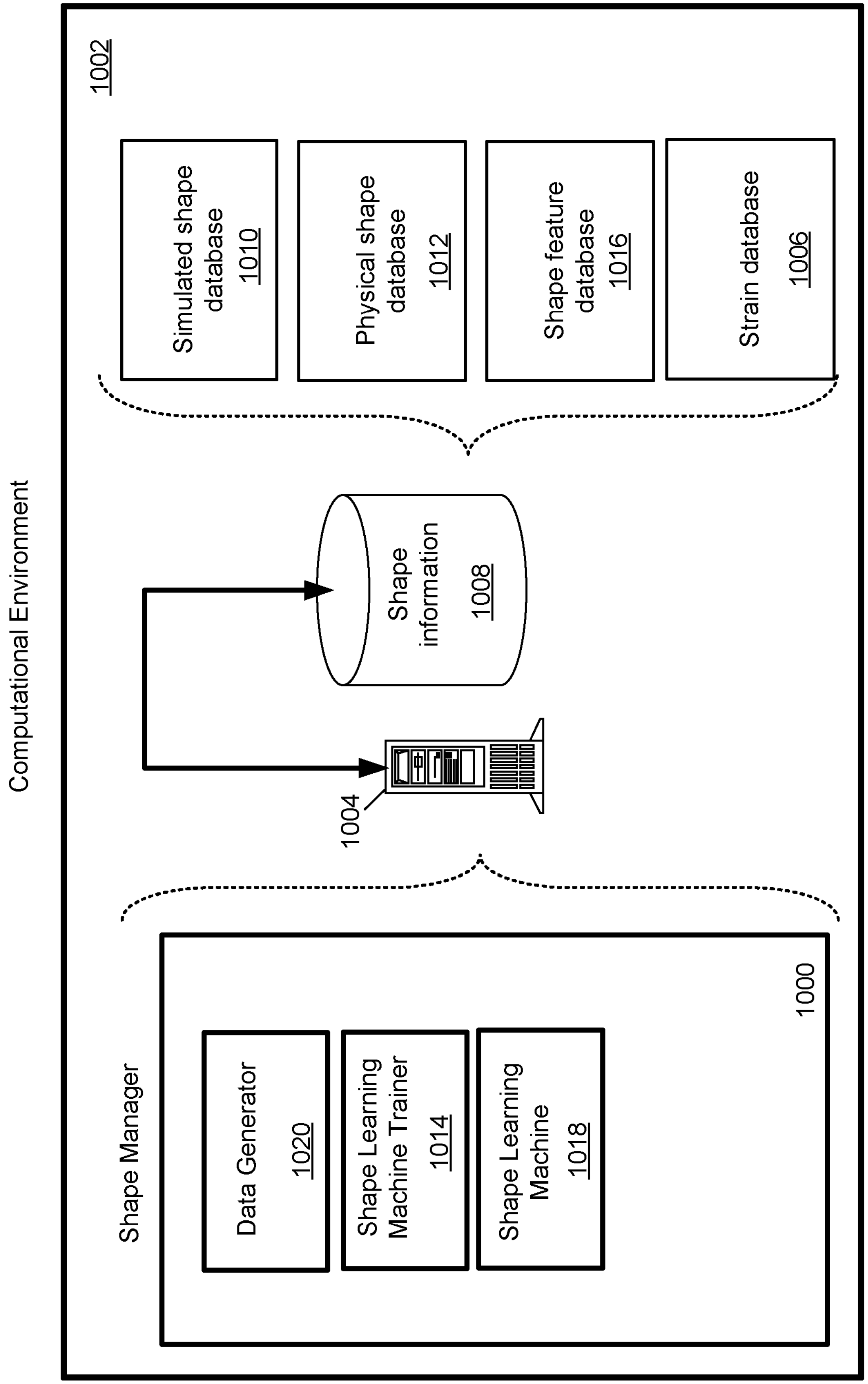
FIG. 10 is a computational system that determines shape information.

Illustrated in FIG. 10, the shape manager 1000 (which includes a number of modules) is executed by the server 1004 present at a computational environment 1002. In this arrangement, the shape manager 1000 includes a data generator 1020, which can collect training data. In this arrangement, such data may be previously stored (e.g., in a strain database 1006) and retrieved from the storage device 1008. Data representing such shape information may also be retrieved from one or more sources external to the computational environment 1002; for example such information may be attained from one or more storage devices of a shape manager (e.g., an entity separate from the computational environment 1002). Along with strain data, the storage device 1008 (or other storage devices at the computational environment 1002) may contain databases of shapes. For example, the storage device 1008 contains a simulated shape database 1010 containing shape data which is computationally generated (e.g., generated by the method of FIG. 8) and a physical shape database 1012 containing shape data that is physically generated (e.g., generated by the method of FIG. 9). A shape database can include information about numerous previously determined shapes, newly determined shapes, etc. From the information stored in the shape databases 1010, 1012, data may be retrieved for learning machine training and use, e.g., to determine shape information (e.g., the shape of an optical fiber, etc.). For example, the shape databases 1010, 1012 may include data that represents various types of shape information (e.g., rendered shapes, components in the x, y, and z axis, etc.)

To train a learning machine (e.g., implemented as a neural network), the shape manager 1000 includes a shape learning machine trainer 1014 that employs both simulated shapes and physical shapes for training operations. In some arrangements, the trainer 1014 may calculate numerical representations of strain data (e.g., in vector form) for machine training.

As illustrated in FIG. 10, the shape learning machine trainer 1014 may also provide other types of functionality. For example, the shape learning machine trainer 1014 may store shape features (e.g., calculated feature vectors) in a shape feature database 1016 for later retrieval and use. Such shape feature data may be attained from sources other than the shape learning machine trainer 1014. For example, the shape learning machine 1018 may similarly store data representing shape features in the shape feature database 1016. In some arrangements, such shape features may be directly provided to the shape learning machine trainer 1014, the shape learning machine 1018, etc. and correspondingly stored in the shape feature database 1016. In other arrangements, calculations may be executed by the shape learning machine trainer 1014, the shape learning machine 1018, etc. to produce the shape features prior to being stored in the shape feature database 1016. For example, numerical values representing one or more shape features (e.g., feature vectors) may be computed from strain data by the shape learning machine trainer 1014, the shape learning machine 1018, etc. As illustrated in the figure, such stored shape feature data may reside in the storage device 1008 (e.g., in the shape feature database 1016). Such shape feature data may be provided to or received from other locations internal or external to the computational environment 1002. For example, the data may be provided for further analysis, storage, etc. to other systems remotely located from the computational environment 1002.

In general, the shape learning machine trainer 1014 may employ one or more techniques to produce the shape learning machine 1018 (e.g., a neural network). For example, the strain data for each shape in the shape databases may be used to define a function. By determining a shape from the provided strain data, the shape learning machine 1018 may be trained.

Once trained, the shape learning machine 1018 may be used to determine the shape of an optical fiber based on strain data (not used to train the machine). For example, strain data may be provided to the shape learning machine 1018. For example, numerical representations (e.g., vectors) of the strain data may be input and the shape learning machine 1018 may calculate a shape components for the optical fiber (e.g., components x(s), y(s), and z(s) of the shape). From the calculated shape components the shape learning machine 818 can render a 3D representation of the shape.

In the illustrated example shown in FIG. 10, the functionality of the data generator 1004, the shape learning machine trainer 1014, and the shape learning machine 1018 are presented as being included in the shape manager 1000. However, in some arrangements, the functionality of one or more of these modules may be provided external from the computational environment 1002. Similarly, the simulated shape database 1010, physical shape database 1012, and shape feature database 1016 are stored in the storage device 1008 in this example. However, one or more of these databases may be stored external to the storage device 1008 and in some arrangements one or more of the databases may be stored external to the computational environment 1002. In some arrangements, the shape manager 1000 may be implemented in software, hardware, or combinations of hardware and software. Similarly the modules included in the shape manager 1000 may individually be implemented in hardware and/or software. One or more database techniques (e.g., structural representations, etc.) may be employed for storing the databases 1010, 1012, 1016.

Figure 11:
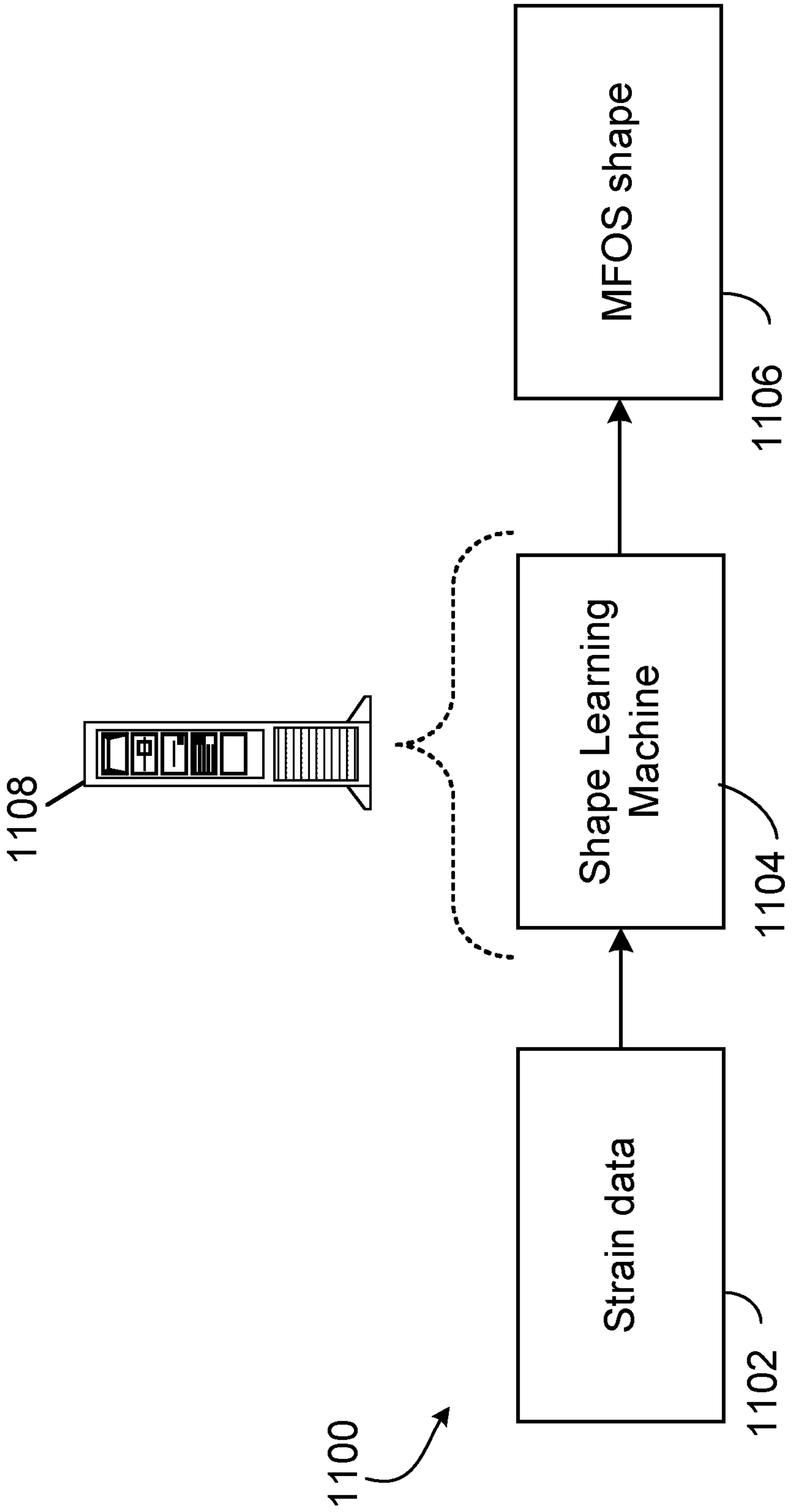
FIG. 11 is a data flow of operations of a shape learning machine.

FIG. 11 is a data flow for a method 1100 representing operations of a shape learning machine after being initially trained. As described above, training data can be employed from a number of sources; for example, simulated shapes (e.g., such as data generated from a method such as the method represented in a flowchart 800 shown in FIG. 8), physical shapes (e.g., such as data generated from a method such as the method represented in a flowchart 900 shown in FIG. 9), both simulated shapes and a physical MFOS, etc. can be used to generate the training data. Strain data 1102 can be provided to the shape learning machine 1104, which is executed by a computer system 1108. The shape learning machine 1104 can determine a shape of the MFOS from the strain data. FIG. 11 represents strain data 1102 being input into the shape learning machine 1104 and producing an output 1106 that represents how the MFOS is shaped. In some arrangements, additional information may also be entered into the shape learning machine 1104, such as initial conditions. The output 1106 can include a function of x(s), y(s) and z(s). Also, a value that represents a confidence level may be output for each of the functions (e.g., ranging from a level of 0.0 to 1.0). In some arrangements, the output 1106 can be a 3-D rendering of an MFOS.

Figure 12:
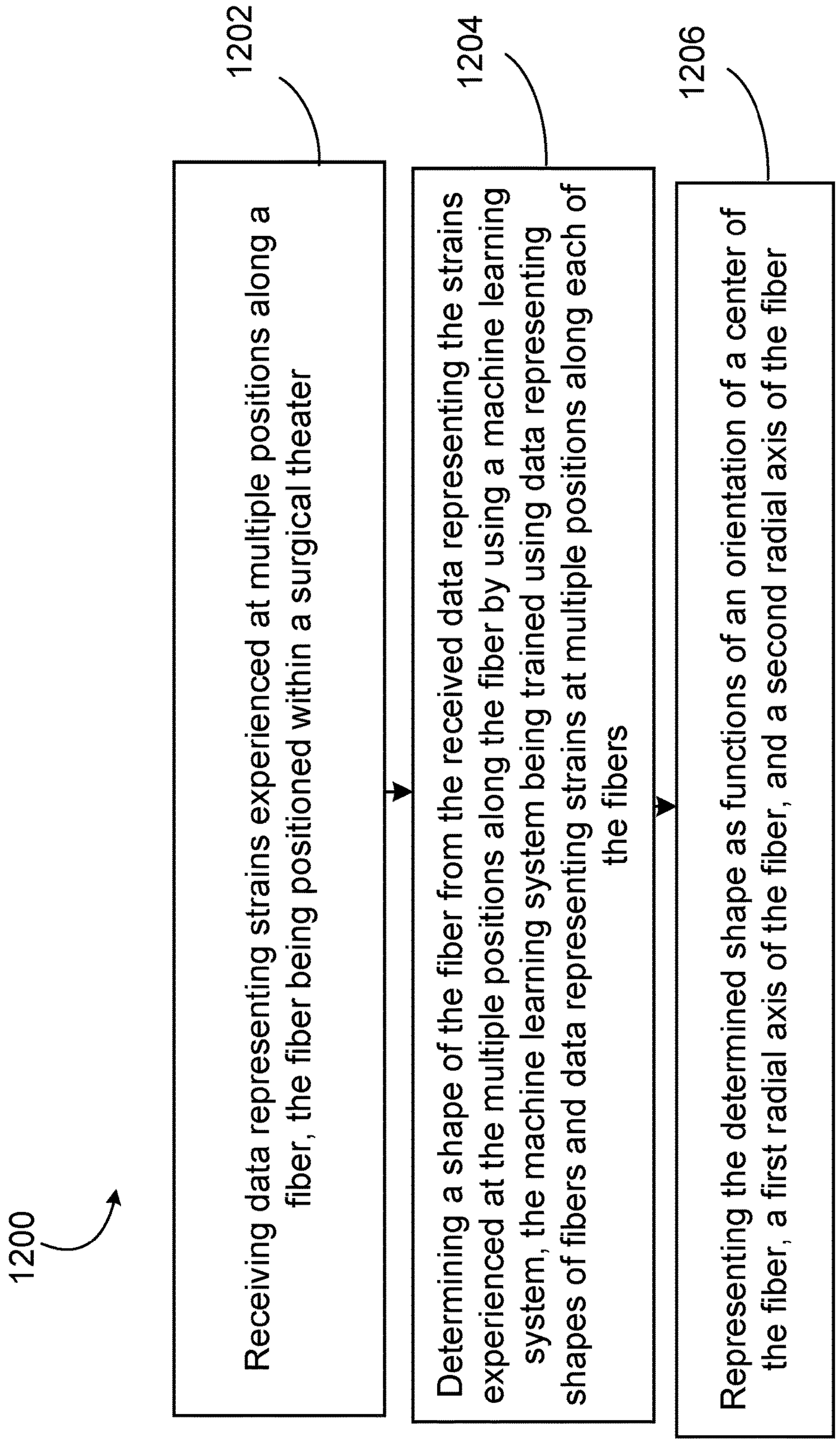
FIG. 12 is a flowchart of operations of a shape learning machine.

FIG. 12 is a flowchart 1200 representing operations of a shape manager (e.g., the shape manager 1000 shown in FIG. 10) after being initially trained. Operations of the shape manager are typically executed by a single computing device (e.g., the server 1006); however, operations of the shape manager may be executed by multiple computing devices. Along with being executed at a single site (e.g., the computational environment 1002), the execution of operations may be distributed among two or more locations.

Operations of the shape manager can include receiving data representing strains experienced at multiple positions along a fiber, the fiber being positioned within a surgical theater (1202). For example, the data can be received from techniques using FBG, Rayleigh scattering, both, etc., as described with reference to FIG. 1. The fiber can be included in a guidewire 112 as described with reference to FIG. 1.

The operations can also include determining a shape of the fiber from the received data representing the strains experienced at the multiple positions along the fiber by using a machine learning system, the machine learning system being trained using data representing shapes of fibers and data representing strains at multiple positions along each of the fibers (1204). For example, determining the shape can include utilizing training data as described with reference to FIG. 11. The machine learning system can include the shape manager 1000 shown in FIG. 10. The data representing shapes of fibers and the data representing strains at multiple positions along each of the fibers can include data which is computationally generated (e.g., generated by the method described with reference to FIG. 8) and data that is physically generated (e.g., generated by the method described with reference to FIG. 9). A neural network or other type of machine learning system may be trained with a cost function such that a shape may be accurately determined from strain data not previously introduced (e.g., not used to train the machine learning system) or for strain data that was previously used for training the machine learning system.

The operations can also include representing the determined shape as functions of an orientation of a center of the fiber, a first radial axis of the fiber, and a second radial axis of the fiber (1206). For example, with reference to FIG. 4, T(s) defines the orientation of the center of the MFOS at each point s. N(s) defines a radial axis of the MFOS, perpendicular to T(s) at each point s. B(s) defines another radial axis of the MFOS, perpendicular to T(s) and N(s) at each point s.

Figure 13:
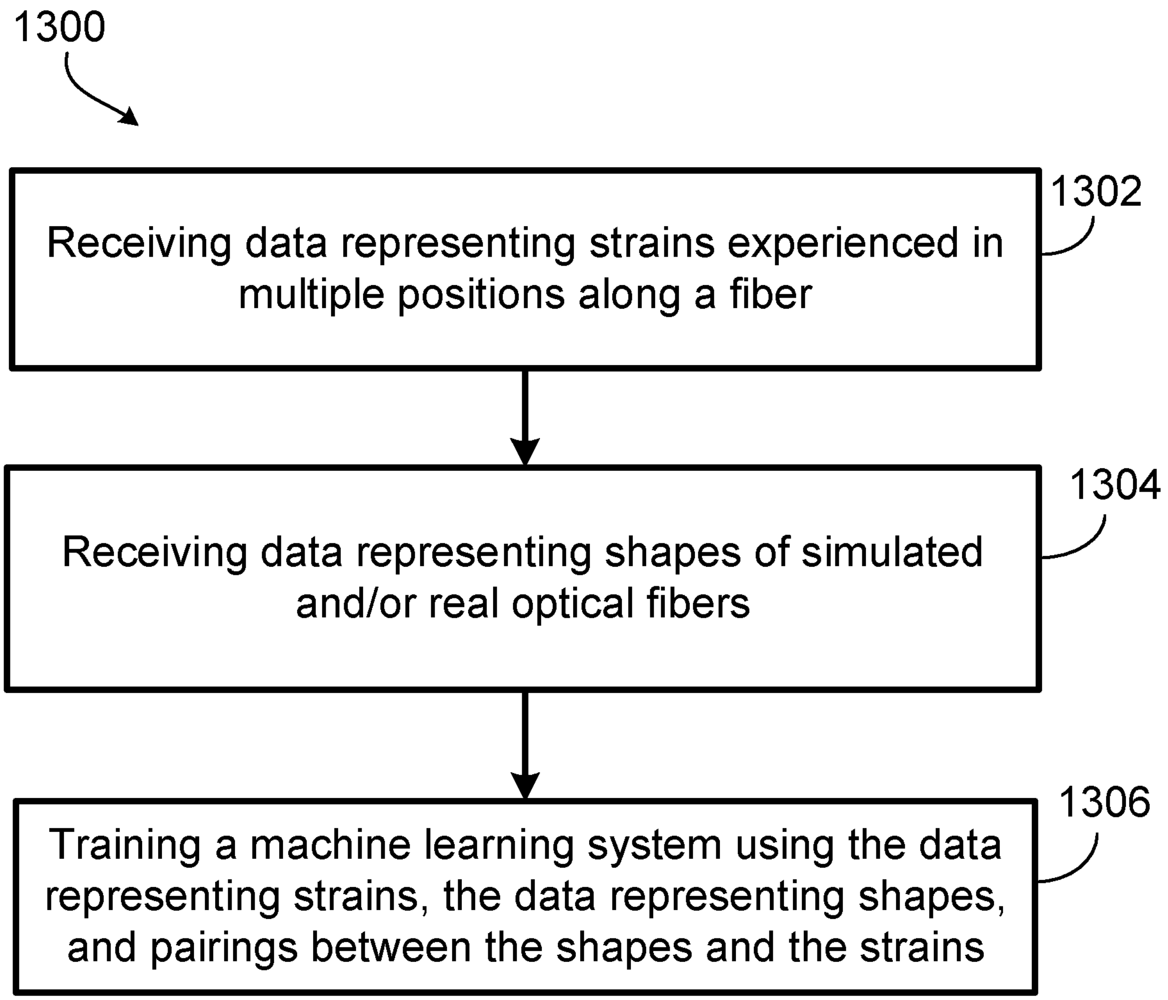
FIG. 13 is a flowchart of operations of a shape manager.

Regarding FIG. 13, a flowchart 1300 represents operations of a shape manager (e.g., the shape manager 1000 shown in FIG. 10). Operations of the shape manager are typically executed by a single computing device (e.g., the server 1006); however, operations of the shape manager may be executed by multiple computing devices. Along with being executed at a single site (e.g., the computational environment 1002), the execution of operations may be distributed among two or more locations.

Operations of the shape manager may include receiving data representing strains experienced in multiple positions along a fiber (1302). For example, data representing the strain (e.g., phase, amplitude, etc.) may be received for one or more fibers being used for training a machine learning system such as the shape learning machine 1018 (shown in FIG. 10). In some arrangements, the data for each strain can be represented as a vector of strain data. Each vector may include numerical values that represent the light (e.g., amplitude, phase, etc.) representative of the strain of the corresponding optical fiber. Operations may also include receiving data representing shapes of simulated and/or physical optical fibers (1304). For example, shape data may be provided in the form of simulated shapes (e.g., as described with reference to FIG. 8) and/or in the form of measured shapes (e.g., as described with reference to FIG. 6). Operations may also include training a machine learning system using the data representing strains, the data representing shapes, and pairings between the shapes and strains (1306). For example, a set of strain data can be paired with data representing the shapes, so that the strain data is representative of that shape. A neural network or other type of machine learning system may be trained with a function such that a shape may be accurately estimated from strain data not previously introduced (e.g., not used to train the machine learning system) or from strain data which was previously used for training the machine learning system.

Figure 14:
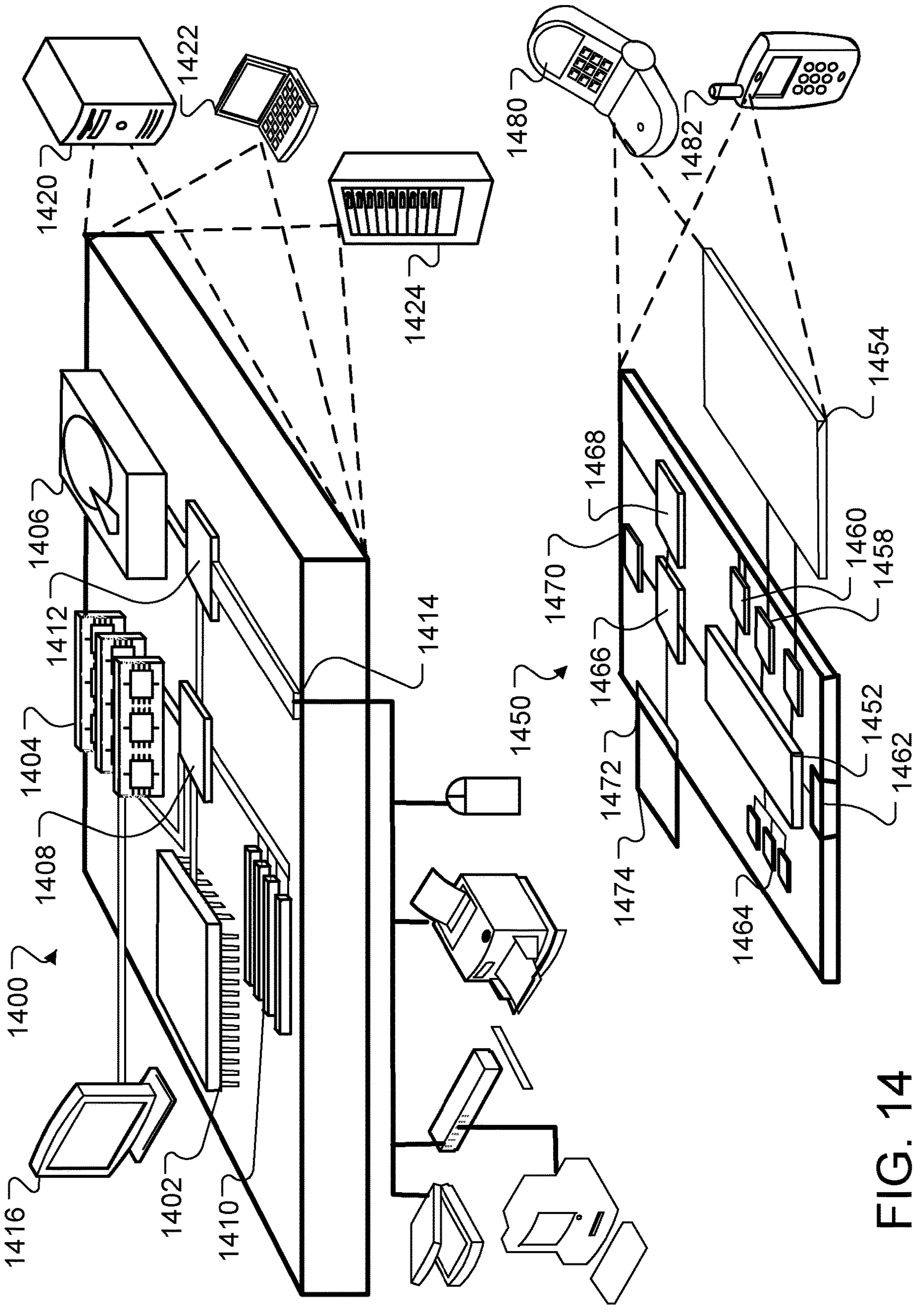
FIG. 14 illustrates an example of a computing device and a mobile computing device that can be used to implement the techniques described.

FIG. 14 shows an example computing device 1400 and an example mobile computing device 1450, which can be used to implement the techniques described herein. For example, the computing device 1400 may be implemented as the computer system 128 of FIG. 1. Computing device 1400 is intended to represent various forms of digital computers, including, e.g., laptops, desktops, workstations, personal digital assistants, servers, blade servers, mainframes, and other appropriate computers. Computing device 1450 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 1400 includes processor 1402, memory 1404, storage device 1406, high-speed interface 1408 connecting to memory 1404 and high-speed expansion ports 1410, and low speed interface 1412 connecting to low speed bus 1414 and storage device 1406. Each of components 1402, 1404, 1406, 1408, 1410, and 1412, are interconnected using various busses, and can be mounted on a common motherboard or in other manners as appropriate. Processor 1402 can process instructions for execution within computing device 1400, including instructions stored in memory 1404 or on storage device 1406, to display graphical data for a GUI on an external input/output device, including, e.g., display 1416 coupled to high-speed interface 1408. In some implementations, multiple processors and/or multiple buses can be used, as appropriate, along with multiple memories and types of memory. In addition, multiple computing devices 1400 can be connected, with each device providing portions of the necessary operations (e.g., as a server bank, a group of blade servers, a multi-processor system, etc.).

Memory 1404 stores data within computing device 1400. In some implementations, memory 1404 is a volatile memory unit or units. In some implementation, memory 1404 is a non-volatile memory unit or units. Memory 1404 also can be another form of computer-readable medium, including, e.g., a magnetic or optical disk.

Storage device 1406 is capable of providing mass storage for computing device 1400. In some implementations, storage device 1406 can be or contain a computer-readable medium, including, e.g., a floppy disk device, a hard disk device, an optical disk device, a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 1404, storage device 1406, memory on processor 1402, and the like.

High-speed controller 1408 manages bandwidth-intensive operations for computing device 1400, while low speed controller 1412 manages lower bandwidth-intensive operations. Such allocation of functions is an example only. In some implementations, high-speed controller 1408 is coupled to memory 1404, display 1416 (e.g., through a graphics processor or accelerator), and to high-speed expansion ports 1410, which can accept various expansion cards (not shown). In some implementations, the low-speed controller 1412 is coupled to storage device 1406 and low-speed expansion port 1414. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router (e.g., through a network adapter).

Computing device 1400 can be implemented in a number of different forms, as shown in FIG. 14. For example, the computing device 1400 can be implemented as standard server 1420, or multiple times in a group of such servers. The computing device 1400 can also can be implemented as part of rack server system 1424. In addition or as an alternative, the computing device 1400 can be implemented in a personal computer (e.g., laptop computer 1422). In some examples, components from computing device 1400 can be combined with other components in a mobile device (e.g., the mobile computing device 1450). Each of such devices can contain one or more of computing device 1400, 1450, and an entire system can be made up of multiple computing devices 1400, 1450 communicating with each other.

Computing device 1450 includes processor 1452, memory 1464, and an input/output device including, e.g., display 1454, communication interface 1466, and transceiver 1468, among other components. Device 1450 also can be provided with a storage device, including, e.g., a microdrive or other device, to provide additional storage. Components 1450, 1452, 1464, 1454, 1466, and 1468, may each be interconnected using various buses, and several of the components can be mounted on a common motherboard or in other manners as appropriate.

Processor 1452 can execute instructions within computing device 1450, including instructions stored in memory 1464. The processor 1452 can be implemented as a chipset of chips that include separate and multiple analog and digital processors. The processor 1452 can provide, for example, for the coordination of the other components of device 1450, including, e.g., control of user interfaces, applications run by device 1450, and wireless communication by device 1450.

Processor 1452 can communicate with a user through control interface 1458 and display interface 1456 coupled to display 1454. Display 1454 can be, for example, a TFT LCD (Thin-Film-Transistor Liquid Crystal Display) or an OLED (Organic Light Emitting Diode) display, or other appropriate display technology. Display interface 1456 can comprise appropriate circuitry for driving display 1454 to present graphical and other data to a user. Control interface 1458 can receive commands from a user and convert them for submission to processor 1452. In addition, external interface 1462 can communicate with processor 1442, so as to enable near area communication of device 1450 with other devices. External interface 1462 can provide, for example, for wired communication in some implementations, or for wireless communication in some implementations. Multiple interfaces also can be used.

Memory 1464 stores data within computing device 1450. Memory 1464 can be implemented as one or more of a computer-readable medium or media, a volatile memory unit or units, or a non-volatile memory unit or units. Expansion memory 1474 also can be provided and connected to device 1450 through expansion interface 1472, which can include, for example, a SIMM (Single In Line Memory Module) card interface. Such expansion memory 1474 can provide extra storage space for device 1450, and/or may store applications or other data for device 1450. Specifically, expansion memory 1474 can also include instructions to carry out or supplement the processes described above and can include secure data. Thus, for example, expansion memory 1474 can be provided as a security module for device 1450 and can be programmed with instructions that permit secure use of device 1450. In addition, secure applications can be provided through the SIMM cards, along with additional data, including, e.g., placing identifying data on the SIMM card in a non-hackable manner.

The memory 1464 can include, for example, flash memory and/or NVRAM memory, as discussed below. In some implementations, a computer program product is tangibly embodied in a data carrier. The computer program product contains instructions that, when executed, perform one or more methods. The data carrier is a computer- or machine-readable medium, including, e.g., memory 1464, expansion memory 1474, and/or memory on processor 1452, which can be received, for example, over transceiver 1468 or external interface 1462.

Device 1450 can communicate wirelessly through communication interface 1466, which can include digital signal processing circuitry where necessary. Communication interface 1466 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 1468. In addition, short-range communication can occur, including, e.g., using a Bluetooth®, WiFi, or other such transceiver (not shown). In addition, GPS (Global Positioning System) receiver module 1470 can provide additional navigation- and location-related wireless data to device 1450, which can be used as appropriate by applications running on device 1450.

Device 1450 also can communicate audibly using audio codec 1460, which can receive spoken data from a user and convert it to usable digital data. Audio codec 1460 can likewise generate audible sound for a user, including, e.g., through a speaker, e.g., in a handset of device 1450. Such sound can include sound from voice telephone calls, recorded sound (e.g., voice messages, music files, and the like) and also sound generated by applications operating on device 1450.

Computing device 1450 can be implemented in a number of different forms, as shown in FIG. 14. For example, the computing device 1450 can be implemented as cellular telephone 1480. The computing device 1450 also can be implemented as part of smartphone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system. This includes at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described herein can be implemented on a computer having a display device (e.g., a CRT (cathode ray tube) or LCD (liquid crystal display) monitor) for presenting data to the user, and a keyboard and a pointing device (e.g., a mouse or a trackball) by which the user can provide input to the computer. Other kinds of devices can be used to provide for interaction with a user as well. For example, feedback provided to the user can be a form of sensory feedback (e.g., visual feedback, auditory feedback, or tactile feedback). Input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such backend, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the components described herein can be separated, combined or incorporated into a single or combined component. The components depicted in the figures are not intended to limit the systems described herein to the software architectures shown in the figures.

A number of embodiments have been described. Nevertheless, it will be understood that various modifications may be made without departing from the spirit and scope of the disclosure. Accordingly, other embodiments are within the scope of the following claims.

What is claimed is:

1. A computing device implemented method comprising:

receiving data from reflected light of a fiber and from reflected light of a reference path, the data representing strains experienced at multiple positions along the fiber, the fiber being positioned within a surgical theater;

determining a shape of the fiber from the received data from the reflected light of the fiber and from the reflected light of the reference path and representing the strains experienced at the multiple positions along the fiber by using a machine learning system, the machine learning system being trained using data representing shapes of fibers and data representing strains at multiple positions along each of the fibers; and representing the determined shape as functions of:

an orientation of a center of the fiber, a first radial axis of the fiber, and a second radial axis of the fiber.

2. The computing device implemented method of claim 1, wherein the data includes a magnitude and phase shift of reflected light along the fiber.

3. The computing device implemented method of claim 1, wherein receiving the data comprises receiving two different polarizations of the reflected light of the fiber and the reflected light of the reference path.

4. The computing device implemented method of claim 1, wherein the fiber is one of a plurality of fibers within a multiple optical fiber sensor, and the method further comprises determining an overall shape of the multiple optical fiber sensor.

5. The computing device implemented method of claim 1, wherein the fiber includes one or more Fiber Bragg Gratings to provide return signals that represent the strain.

6. The computing device implemented method of claim 1, wherein the reference path is a fixed path.

7. The computing device implemented method of claim 1, wherein receiving the data representing the strains experienced at the multiple positions along the fiber comprises receiving an interference pattern generated from the reflected light of the reference path and the reflected light reflected of the fiber.

8. The computer device implemented method of claim 1, wherein the multiple positions are equally spaced along the fiber.

9. The computer device implemented method of claim 1, wherein the training data comprises simulated data.

10. The computer device implemented method of claim 9, wherein the training data comprises simulated data and physical data collected from one or more optical fibers.

11. A system comprising:

a computing device comprising:

a memory configured to store instructions; and a processor to execute the instructions to perform the operations comprising:

receiving data from reflected light of a fiber and from reflected light of a reference path, the data representing strains experienced at multiple positions along the fiber, the fiber being positioned within a surgical theater;

determining a shape of the fiber from the received data from the reflected light of the fiber and from the reflected light of the reference path and representing the strains experienced at the multiple positions along the fiber by using a machine learning system, the machine learning system being trained using data representing shapes of fibers and data representing strains at multiple positions along each of the fibers; and representing the determined shape as functions of:

an orientation of a center of the fiber, a first radial axis of the fiber, and a second radial axis of the fiber.

12. The system of claim 11, wherein the data includes a magnitude and phase shift of reflected light along the fiber.

13. The system of claim 11, wherein receiving the data comprises receiving two different polarizations of the reflected light of the fiber and the reflected light of the reference path.

14. The system of claim 11, wherein the fiber is one of a plurality of fibers within a multiple optical fiber sensor, and the method further comprises determining an overall shape of the multiple optical fiber sensor.

15. The system of claim 11, wherein the fiber includes one or more Fiber Bragg Gratings to provide return signals that represent the strain.

16. One or more computer readable media storing instructions that are executable by a processing device, and upon such execution cause the processing device to perform operations comprising:

receiving data from reflected light of a fiber and from reflected light of a reference path, the data representing strains experienced at multiple positions along the fiber, the fiber being positioned within a surgical theater;

determining a shape of the fiber from the received data from the reflected light of the fiber and from the reflected light of the reference path and representing the strains experienced at the multiple positions along the fiber by using a machine learning system, the machine learning system being trained using data representing shapes of fibers and data representing strains at multiple positions along each of the fibers; and representing the determined shape as functions of:

an orientation of a center of the fiber, a first radial axis of the fiber, and a second radial axis of the fiber.

17. The computer readable media of claim 16, wherein the data includes a magnitude and phase shift of reflected light along the fiber.

18. The computer readable media of claim 16, wherein receiving the data comprises receiving two different polarizations of the reflected light of the fiber and the reflected light of the reference path.

19. The computer readable media of claim 16, wherein the fiber is one of a plurality of fibers within a multiple optical fiber sensor, and the method further comprises determining an overall shape of the multiple optical fiber sensor.

20. The computer readable media of claim 16, wherein the fiber includes one or more Fiber Bragg Gratings to provide return signals that represent the strain.

* * * * *